(12) United States Patent
Takahashi et al.

(10) Patent No.: US 6,414,710 B1
(45) Date of Patent: Jul. 2, 2002

(54) ELECTRONIC ENDOSCOPE

(75) Inventors: Tadashi Takahashi, Saitama; Ryo Ozawa, Tokyo, both of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/337,338

(22) Filed: Jun. 21, 1999

(30) Foreign Application Priority Data

Jun. 22, 1998 (JP) .......................................... 10-174417

(51) Int. Cl.[7] .............................. A61B 1/06; A61B 1/04; H04N 7/18
(52) U.S. Cl. .......................... 348/69; 600/160; 600/180
(58) Field of Search .............................. 348/65, 68, 69, 348/70; 600/109, 180, 160; H04N 7/18

(56) References Cited

U.S. PATENT DOCUMENTS

| 4,322,129 A | 3/1982 | Takahashi et al. ............ 396/17 |
| 5,115,261 A | 5/1992 | Noda et al. ................. 600/181 |
| 5,159,380 A | 10/1992 | Furuya et al. ................ 396/17 |
| 5,184,170 A | 2/1993 | Takahashi et al. ........... 600/180 |
| 5,191,369 A | 3/1993 | Furuya et al. ................ 396/17 |
| 5,257,100 A | 10/1993 | Hattori et al. ................ 348/65 |
| 5,475,420 A | * 12/1995 | Buchin .......................... 348/69 |
| 6,080,104 A | * 6/2000 | Ozawa et al. .................. 348/69 |

FOREIGN PATENT DOCUMENTS

JP          4138127          5/1992

* cited by examiner

*Primary Examiner*—Howard Britton
(74) *Attorney, Agent, or Firm*—Greenblum & Bernstein P.L.C.

(57) ABSTRACT

In an electronic endoscope, a flexible scope has an image sensor provided at a distal end thereof, and an optical light guide extending therethrough. The scope is detachably connectable, at a proximal end thereof, to a processing unit, which processes image-pixel signals successively read from the image sensor. A light source is provided in the processing unit such that light, emitted from the light source, is guided through the guide and radiates from the distal end of the scope. An aperture-stop is associated with the source that regulates the radiation of light from the distal end of the scope. A histogram generator generates a luminance-signal-histogram based on the processed signals. An average luminance level-value is approximately calculated based on luminance signals exhibiting thinned luminance levels extracted from the histogram. The aperture-stop is controlled in accordance with the approximate average luminance level-value, such that an image having a constant brightness level is reproduced based on the processed signals.

11 Claims, 13 Drawing Sheets

ELECTRONIC ENDOSCOPE

BACKGROUND OF THE INVENTION

1. Field of the Invention

This invention relates to an electronic endoscope comprising a flexible conduit or scope and a video-signal processing unit to which the flexible scope is detachably connected at a proximal end.

2. Description of the Related Art

In such an electronic endoscope, the flexible conduit or scope includes an objective lens system provided at the distal end thereof, and a solid image sensor, such as a CCD (charge-coupled-device) image sensor, associated therewith. The flexible scope also includes an optical light guide extended therethrough, formed as a bundle of optical fibers, which is associated with a lighting lens system provided at the distal end of the flexible scope.

On the other hand, the video-signal processing unit includes a white-light source, such as a halogen lamp, a xenon lamp or the like. When the flexible scope is connected to the video-signal processing unit, the proximal end of the optical light guide is optically connected to the light source. Thus, an object to be photographed is illuminated by light radiating from the distal end of the optical light guide, and is focused as an optical image on a light-receiving surface of the CCD image sensor by the objective lens system.

The focused optical image is converted into a frame of analog image-pixel signals by the CCD image sensor. Then, the frame of analog image-pixel signals is read from the CCD image sensor, and is fed to the video-signal processing unit, in which the image-pixel signals are suitably processed, thereby producing a video signal including image-pixel signals and various synchronizing signals. Then, the video signal is fed from the video-signal processing unit to a TV monitor to reproduce the photographed object on the monitor on the basis of the video signal.

In general, the objective lens system, used in the electronic endoscope, exhibits a large depth of focus, because a close-range object image and/or a distant-range object image to be photographed must be focused on the light-receiving surface of the CCD image sensor by the objective lens system, before the photographed close-range object image and/or distant-range object image can be sharply reproduced on the monitor.

In this case, to maintain a constant overall brightness of a reproduced object image on the monitor, the radiation of the illuminating-light from the distal end of the optical light guide should be regulated in accordance with a distance between the photographed object image and the distal end of the optical light guide. For example, when only a medical image of a patient is to be reproduced as a close-up image by placing the distal end of the flexible scope close to the medical image, the radiation of the illuminating-light should be lowered to a minimum level in order to generate the medical image at a predetermined brightness on the monitor. Then, as the distal end of the flexible scope is moved away from the medical image, the radiation of the illuminating-light should be gradually increased from the minimum level to prevent the brightness of the reproduced medical image from being reduced.

Conventionally, for a regulation of radiation of the illuminating-light from the distal end of the optical light guide, an aperture-stop is associated with the white-light source, and is automatically controlled such that an overall brightness of the reproduced object image is always maintained at a constant level. In particular, a frame of luminance signals is extracted from the video signal at given regular time-intervals, and an average luminance level is calculated from the extracted luminance signals. Then, the radiation of the illuminating-light from the distal end of the optical light guide is regulated by controlling the aperture-stop such that the average luminance level coincides with a predetermined reference level.

Nevertheless, in the conventional electronic endoscope, there is room for improvement in a responsiveness of the regulation of the radiation of the illuminating-light from the distal end of the optical light guide, because a calculation time for calculating the average luminance level is relatively long, and because the calculation must be repeated at very short-time intervals. For example, in an electronic endoscope using the NTSC system, the calculation must be repeated at regular time-intervals of $1/30$ sec, and, in an electronic endoscope using the PAL system, the calculation must be repeated at regular time-intervals of $1/25$ sec.

On the other hand, in general, an electronic endoscope is constituted such that a photographed image is reproduced as a color image. In this case, a frame of red image-pixel signals, a frame of green image-pixel and a frame of blue image-pixel signals are cyclically read out from the CCD image sensor, and are then subjected to a white-balance correction processing such that the photographed color image is reproduced on a monitor with a proper color balance. As is well-known, the white-balance correction processing is performed by processing respective gains of red, green and blue image-pixel signals with red, green and blue correction factors, which exhibit inherent values with respect to each individual CCD image sensor used in an electronic endoscope. Thus, the correction factors are determined during manufacture of the electronic endoscope.

In particular, a manufactured flexible scope concerned is connected to a so-called master video-signal processor, and a distal end of the flexible scope is inserted into a tubular-like envelope, an inner wall surface of which is coated with a standard white pigment layer. Then, a frame of red image-pixel signals, a frame green image-pixel signals and a frame of blue image-pixel signals are obtained from the CCD image sensor, and a red correction factor, a green correction factor and a blue correction factor are determined on the basis of the obtained color image-pixel signals such that gains of red, green and blue image-pixel signals are equal to each other.

Nevertheless, an electronic characteristic of the master video-signal processor does not necessarily coincide with that of a manufactured and used video-signal processor to which the flexible endoscope concerned is connected. Thus, the determined correction factors are not necessarily proper with respect to the manufactured and used video-signal processor. Further, the color correction factors should be periodically readjusted and redetermined in accordance with deterioration of a white-light lamp which harmfully affects the white-balance correction processing. Namely, there is a demand for an improved electronic endoscope in which the redetermination of the color correction factors can be easily carried out.

SUMMARY OF THE INVENTION

Therefore, an object of the present invention is to provide an electronic endoscope in which a responsiveness of a regulation of radiation of an illuminating-light from a distal end of an optical light guide can be favorably improved.

Another object of the present invention is to provide an electronic endoscope in which it is possible to easily readjust and redetermine color correction factors for a white-balance correction.

In accordance with the present invention, there is provided an electronic endoscope which comprises a flexible scope, and a video-signal processing unit to which a proximal end of the flexible scope is detachably connected. The flexible scope has an image sensor provided at a distal end of the scope, and an optical light guide extending through the scope. The video-signal processing unit processes image-pixel signals successively read from the image sensor, and is provided with a light source such that light, emitted from the light source, is guided through the optical light guide and radiates from the distal end of the flexible scope. The electronic end scope features a light-emission regulator which may be an aperture-stop associated with the light source, and the aperture-stop regulates the radiation of light from the distal end of the flexible scope. The electronic endoscope further features a histogram generator which successively generates a luminance-signal-histogram in accordance with the processed image-pixel signals, an approximate-calculator which approximately calculates an approximate average luminance level-value in accordance with luminance signals exhibiting thinned luminance levels extracted from the luminance-signal-histogram, and a controller which controls the light-emission regulator in accordance with the approximate average luminance level-value, such that an image having a constant brightness level is reproduced in accordance with the processed image-pixel signals.

The generation of the luminance-signal-histogram by the histogram generator may be based on either a frame or field of image-pixel signals extracted from the processed image-pixel signals. The thinned luminance levels may be obtained by suitably extracting a series of luminance levels from the luminance-signal-histogram at regular intervals. Preferably, the thinned luminance levels are alternately extracted from the luminance-signal-histogram.

The approximate calculation of the average luminance level-value by the calculator may be performed over a restricted range of a full histogram-definition range of the luminance-signal-histogram, and the restricted range may be defined in accordance with another luminance-signal-histogram generated in the histogram-generator prior to the generation of the luminance-signal-histogram. Preferably, the restricted range is obtained by marginally extending a histogram range defined by a minimum luminance level and a maximum luminance level of another luminance-signal-histogram generated in the histogram-generator prior to the generation of the luminance-signal-histogram.

Preferably, the electronic endoscope further comprises an exact-calculator, which periodically and exactly calculates an exact average luminance level-value in accordance with luminance signals included in the luminance-signal-histogram, and the controller periodically controls the light-emission regulator in accordance with the exact average luminance level-value.

The electronic endoscope may be constituted such that a gain-correction factor adjustment mode or white-balance-readjustment mode is selected as an operation mode of the endoscope. In this case, the image sensor successively is constituted so as to generates a first frame of monochromatic image-pixel signals, a second frame of monochromatic image-pixel signals and a third frame of monochromatic image-pixel signals; the flexible scope further has a memory that stores a first gain-correction factor, a second gain-correction factor and a third gain-correction factor; the video-signal processing unit is constituted so as to read the first, second and third gain-correction factors from the memory when the flexible scope is connected to the unit, and so as to process the first, second and third frames of monochromatic image-pixel signals with the first, second and third gain-correction factors, respectively; and the histogram generator is constituted so as to successively generate a first image-pixel-signal-histogram, a second image-pixel-signal-histogram and a third image-pixel-signal-histogram in accordance with the first, second and third frames of monochromatic image-pixel signals, processed with the first gain-correction factor, the second gain-correction factor and the third correction factor, respectively. The electronic endoscope further comprises: a first calculator that calculates a first average signal-level-value in accordance with image-pixel signals included in the first image-pixel-signal-histogram; a second calculator that calculates a second average signal-level-value in accordance with of image-pixel signals included in the second image-pixel-signal-histogram; a third calculator that calculates a third average signal-level-value in accordance with of image-pixel signals included in the third image-pixel-signal-histogram; and a gain-correction-factor adjuster that adjusts at least two of the first, second and third gain-correction factors such that the first, second and third average signal-level-values are substantially equal to each other.

Preferably, the electronic endoscope comprises a writer which writes the adjusted gain-correction factors in the memory of the flexible scope. Also, the electronic endoscope preferably comprises an operation-mode selector an operation-mode selector that switches an operation mode of the endoscope from a usual-operation mode to the gain-correction factor adjustment mode, and the adjustment of the gain-correction factors by the gain-correction-factor adjuster is performed when the gain-correction factor adjustment mode or white-balance-readjustment mode is selected by the operation-mode selector.

BRIEF DESCRIPTION OF THE DRAWINGS

These objects and other objects of the present invention will be better understood from the following description, with reference to the accompanying drawings in which.

DESCRIPTION OF THE PREFERRED EMBODIMENT

Figure 1:
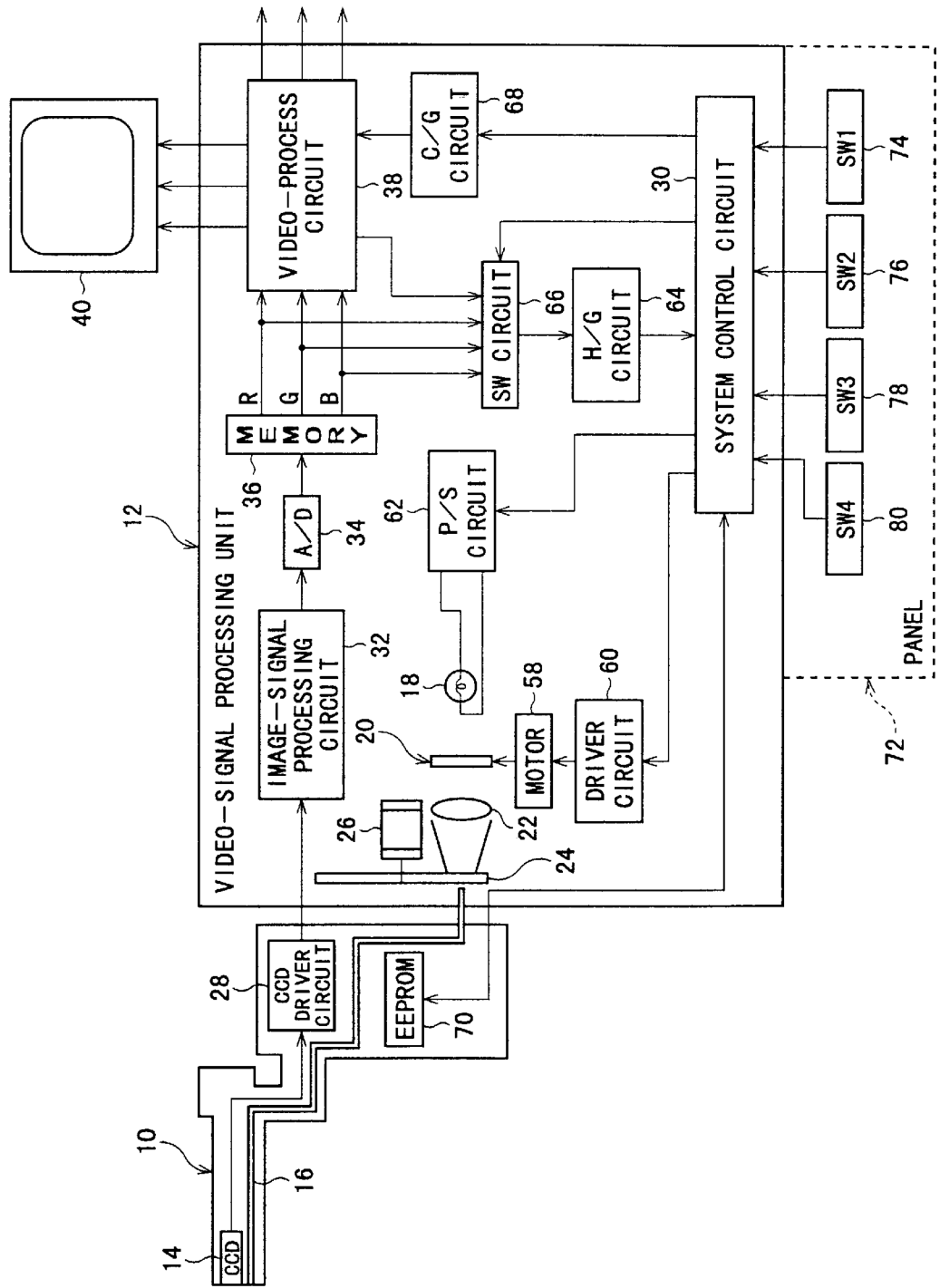
FIG. 1 is a schematic block diagram of an electronic endoscope according to the present invention.

With reference to FIG. 1, an electronic endoscope according to the present invention is shown as a block diagram. The electronic endoscope comprises a flexible conduit or scope 10, and a video-signal processing unit 12 to which the flexible scope 10 is detachably attached.

The flexible scope 10 includes an objective lens system (not shown) provided at the distal end thereof, and a solid image sensor 14, such as a CCD (charge-coupled-device) image sensor, associated therewith. An optical object to be photographed is focused, as an optical image, on a light-receiving surface of the CCD image sensor 14 by the objective lens system.

The flexible scope 10 also includes an optical light guide 16 extended therethrough and formed as a bundle of optical fibers. The optical light guide 16 terminates at a light-radiating end face at the distal end of the flexible scope 10, and is associated with a lighting lens system (not shown) provided thereat. When the flexible scope 10 is connected to the video-signal processing unit 12, the proximal end of the optical light guide 16 is optically connected to a white-light source 18, such as a halogen lamp, a xenon lamp or the like, provided in the video-signal processing unit 12. The light, emitted from the white-light source or lamp 18, is directed to the proximal end of the optical light guide 16, and then radiates as an illuminating-light from the distal end of the optical light guide 16.

As shown in FIG. 1, an aperture-stop 20 and a condenser lens 22 are provided between the white-light lamp 18 and the proximal end of the optical light guide 16. The aperture-stop 20 is used to adjust an amount of the light directed from the lamp 18 to the proximal end of the optical light guide 16, i.e. an amount of the illuminating-light radiating from the distal end of the optical light guide 16. The condenser lens 22 is used to converge the light, emitted from the lamp 18, on the proximal end of the optical light guide 16.

In this embodiment, for reproduction of a photographed image as a color image, an RGB field sequential-type color imaging system is incorporated in the electronic endoscope. Thus, a rotary RGB color filter disk 24 is interposed between the white-light lamp 18 and the proximal end of the optical light guide 16 of the video-signal processing unit 12.

Figure 2:
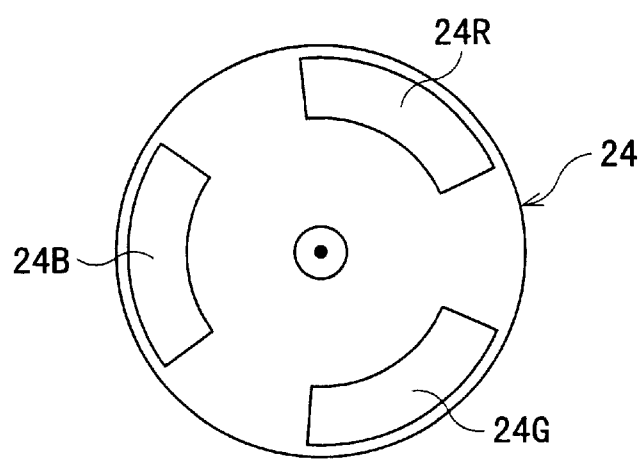
FIG. 2 is a front view of a rotary RGB color filter disk used in the electronic endoscope of FIG. 1.

As shown in FIG. 2, the rotary RGB color filter disk 24 has three sector-shaped color filters, i.e. a red filter 24R, a green filter 24G and a blue filter 24B, and these color filters 24R, 24G and 24B are circumferentially and uniformly arranged such that three centers of the color filters 24R, 24G and 24B are spaced from each other at regular angular-intervals of 120 degrees. A sector area between two adjacent color filters (24R and 24G; 24G and 24B; or 24B and 24R) serves as a light-shielding area.

Figure 3:
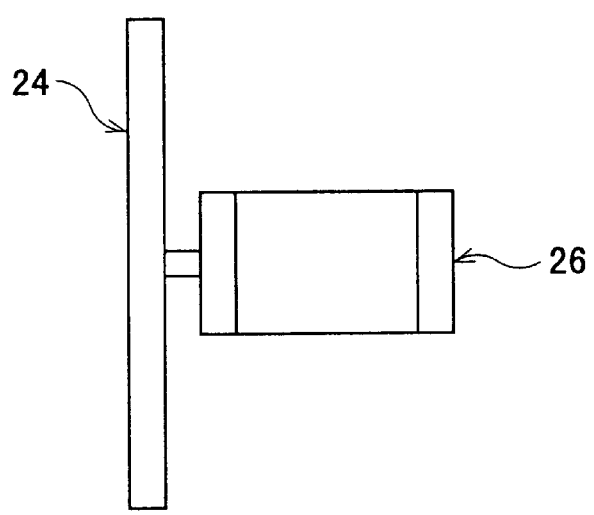
FIG. 3 is a side view of the rotary RGB color filter disk block mounted on a shaft of an electric motor.

As shown in FIG. 3, the rotary RGB color filter disk 24 is rotated by an electric motor 26, such as a servo-motor, a stepping motor or the like, at a given rotational frequency in accordance with a used image-reproduction method, such as the NTSC system, the PAL system or the like, whereby an optical object to be photographed is sequentially illuminated by red light, green light and blue light. In particular, in the NTSC system, the rotational frequency of the color filter disk 24 is 30 Hz, and, in the PAL system, the rotational frequency of the color filter disk 24 is 25 Hz.

For example, in the NTSC system, the color filter disk 24 makes one revolution over a time period of $\frac{1}{30}$ sec, and thus the light, emitted from the lamp 18, passes through each of the color filters 24R, 24G and 24B over a time period of $\frac{1}{180}$ sec. Namely, a red light, green light and a blue light intermittently and cyclically radiate from the distal end of the optical light guide 16, and a red optical image, a green optical image and a blue optical image are sequentially and cyclically focused on the light-receiving surface of the CCD image sensor 14.

Each of the red, green and blue optical images is sequentially converted into a frame of monochromatic (red, green, blue) analog image-pixel signals by the CCD image sensor 14, and the monochromatic (red, green, blue) analog image-pixel signals are successively read from the CCD image sensor 14 over consecutive light-shielding time periods corresponding to the light-shielding areas between two adjacent color filters (24R and 24G; 24G and 24B; or 24B and 24R). The reading of the monochromatic (red, green, blue) analog image-pixel signals from the CCD image sensor 14 is performed in accordance with a series of clock pulses, having a given frequency, output from a CCD driver circuit 28 provided in the flexible scope 10.

As shown in FIG. 1, the video-signal processing unit 12 is provided with a system control circuit 30, which may be constituted as a microcomputer, used to control the electronic endoscope as a whole, comprising, for example, a central processing unit (CPU), a read-only memory (ROM) for storing programs and constants, a random-access memory (RAM) for storing temporary data, and an input/output interface circuit (I/O).

The video-signal processing unit 12 is provided with an image-signal processing circuit 32, which is connected to the CCD driver circuit 28 when the flexible scope 10 is attached to the video-signal processing unit 12. The monochromatic analog image-pixel signals, read from the CCD image sensor 14 by the CCD driver circuit 28, are fed to the image-signal processing circuit 32, in which the monochromatic image-pixel signals are subjected to various image-processings, such as a white-balance correction processing, a gamma-correction processing, a profile-enhancing processing and so on. Note, the reading of the monochromatic image-pixel signals from the CCD image sensor 14 by the CCD driver circuit 28 and the processing of the monochromatic image-pixel signals in the image-signal processing circuit 32 are performed under control of the system control circuit 30.

The monochromatic analog image-pixel signals, suitably processed in the image-signal processing circuit 32, are fed to an analog-to-digital (A/D) converter 34, and are converted by the A/D converter 34 into monochromatic digital image-pixel signals which are temporarily stored in a frame memory 36. In this frame memory 36, three frame memory sections are defined for the storage of red digital image-pixel signals, green digital image-pixel signals and blue digital image-pixel signals, respectively. In short, the monochromatic digital image-pixel signals are stored in a corresponding frame memory section defined in the frame memory 36.

Then, the respective red, green and blue digital image-pixel signals are simultaneously read from the three frame memory sections of the frame memory 36, and are output to a video-process circuit 38, as a red digital video signal R, a green digital video signal G and a blue digital video signal B, respectively. Namely, each of the red, green and blue digital video signals R, G and B is produced by suitably adding various synchronizing signals to the monochromatic (red, green, blue) digital image-pixel signals read from the frame memory 36.

In the video-process circuit 38, the red digital video signal R, the green digital video signal G and the blue digital video signal B are converted into a red analog video signal, a green analog video signal and a blue analog video signal, respectively, and each of the red, green and blue analog video signals is processed such that a high frequency noise component is eliminated therefrom. Then, the red, green and blue analog video signals are output from the video process circuit 38 to a monitor 40 to thereby reproduce and display the photographed color image thereon.

Also, the video-process circuit 38 includes a color encoder for producing various types of color digital video signals on the basis of the red, green and blue digital video signals, and the various types of video color digital signals are output from the video-process circuit 38 to various pieces of peripheral equipment (not shown), such as a remote monitor, a video tape recorder, a printer, an image-processing computer and so on.

Figure 4:
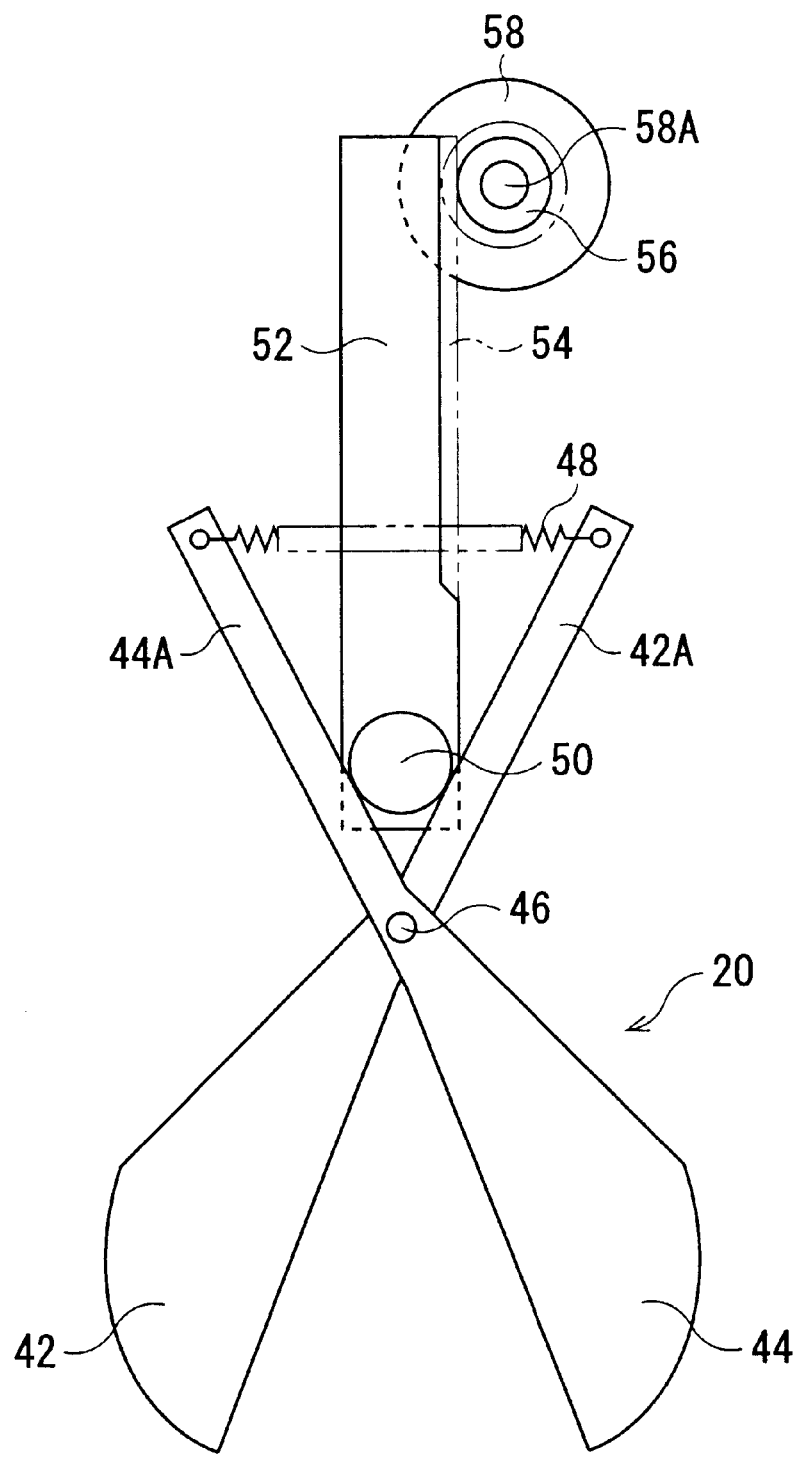
FIG. 4 is a front view of an aperture-stop with a drive mechanism thereof, used in the electronic endoscope of FIG. 1.

As shown in FIG. 4, the aperture-stop 20 comprises a pair of blade elements 42 and 44, each of which has an arm portion (42A, 44A) integrally extended therefrom. The blade elements 42 and 44 are crossed, and are rotatably connected to each other by a pivot pin 46 at the crossing point thereof. Note, the pivot pin 46 is securely and suitably supported by a structural frame (not shown) of the video-signal processing unit 12. The arm portions 42A and 44A are connected to each other by a tensile coil spring 48, and are engaged with a cam pin 50 provided therebetween. The cam pin 50 is securely attached to a lower end of an elongated plate member 52, which is movably supported by suitable guide members (not shown). The elongated plate member 52 is formed with a rack 54, which engages a pinion 56. The pinion 56 is securely mounted on a drive shaft 58A of an electric drive motor 58 securely supported by the structural frame of the video-signal processing unit 12.

With the arrangement as shown in FIG. 4, when the drive motor 58 is driven such that the elongated plate member 52 is lifted, the blade elements 42 and 44 are moved so as to close on each other. On the contrary, when the drive motor 58 is driven such that the elongated plate member 52 is lowered, the blade elements 42 and 44 are moved so as to separate from each other.

Of course, the aperture-stop 20 is provided in the video-signal processing unit 12 in such a manner that the pair of blade elements 42 and 44 intercepts the emission of the light from the lamp 18. Thus, as the blade elements 42 and 44 are moved so as to be spaced apart from each other, an amount of the light passing between the blade elements 42 and 44 gradually increases, and, as the blade elements 42 and 44 are moved so as to close on each other, an amount of the light passing between the blade elements 42 and 44 is gradually reduced. In short, the radiation of the light from the distal end of the optical light guide 16 is regulated by operating the aperture-stop 20.

As shown in FIG. 1, the electric drive motor 58 is driven by a driver circuit 60, which is operated under control of the system control circuit 30. Also, the white-light lamp 18 is electrically energized by a power source circuit 62, which is operated under control of the system control circuit 30.

Also, as shown in FIG. 1, the video-signal processing circuit 12 features a histogram-generating circuit 64, which is selectively connected to one of the frame memory 36 and the video-process circuit 38 by a switching circuit 66, a switching operation of which is controlled by the system control circuit 30. Usually, the histogram-generating circuit 64 is connected to the video-process circuit 38 to generate a histogram on the basis of a frame or field of luminance signals, which is successively obtained from a component-type video-signal produced in the video-process circuit 38, and the successively-generated luminance-signal-based histogram is used to automatically regulate the radiation of the light from the distal end of the optical light guide 16, as discussed in detail hereinafter.

Note, the histogram generated in the histogram-generating circuit 64 is renewed at a given regular time-interval in accordance with a used image-reproduction method. For example, when the NTSC system is used in the electronic endoscope as shown in FIG. 1, the renewal of the histogram is performed at a regular time-interval of 1/30 sec, and, when the PAL system is used, the renewal of the histogram is performed at a regular time-interval of 1/25 sec.

In the electronic endoscope as shown in FIG. 1, when red, green and blue correction factors for the white-balance correction processing are readjusted and redetermined, the histogram-generating circuit 64 is connected to the frame memory 36 by an operation of the switching circuit 66, and produces a red histogram, a green histogram and a blue histogram on the basis of respective frames or fields of red, green and blue digital image-pixel signals, respectively, which are included in the red, green and blue digital video signals read from the frame memory 36. The produced red, green and blue histograms are utilized for the readjustment and redetermination of the color correction factors for the white-balance correction processing, as discussed in detail hereinafter.

As shown in FIG. 1, the video-signal processing unit 12 further features a character generator circuit 68 including a VRAM memory (not shown). When character code data are written to the VRAM, the character generator 32 generates digital character pattern signals on the basis of the character code data stored in the VRAM, and outputs the digital character pattern signals to the video-process circuit 38, in which the digital character pattern signals are added to the red digital video signal, the green digital video signal and the blue digital video signal.

Of course, when the red, green and blue digital video signals carrying the character pattern signals are converted into red, green and blue analog video signals, and when a photographed color image is reproduced on the monitor 40 on the basis of the converted red, green and blue analog video signals, character information data based on the character pattern signals is displayed on the monitor 40, together with the reproduced color image.

The character information data to be displayed on the monitor 40 is classified into two groups: one group of variable character information data, such as a patient's name, a date and time of medical examination, examination comments and so on; and the other group of fixed character information data concerns fixed messages, such as "ADJUSTMENT FOR WHITE BALANCE IS POSSIBLE", and "ADJUSTMENT OF WHITE BALANCE HAS BEEN COMPLETED", which especially relate to this invention.

The variable character code data corresponding to the variable character information data are written in the VRAM of the character generator circuit 68 through a keyboard (not shown), under control of the system control circuit 30, if necessary. On the other hand, the fixed character code data corresponding to the fixed character information data are previously stored in the ROM of the system control circuit 30. If necessary, the fixed character code data are read from the ROM of the system control circuit 30, and are then written in the VRAM of the character generator circuit 68.

As shown in FIG. 1, the flexible scope 10 is provided with a non-volatile memory, such as an electrically-erasable programmable read-only memory (EEPROM) 70, in which various types of information data is previously stored. For example, an image-pixel number data of the CCD image sensor 14, a clock pulse frequency data and so on are stored in the EEPROM 70. Also, as data which especially relates to this invention, the above-mentioned red, green and blue correction factors for the white-balance correction processing are stored in the EEPROM 70. As is apparent from the foregoing, the color correction factors are previously stored in EEPROM 70 when the flexible scope 10 is manufactured.

As conceptually shown by a dotted line in FIG. 1, the video-signal processing unit 12 has a manipulation panel 72, in which various switches are provided. In this drawing, the switches (SW1, SW2, SW3 and SW4), which especially relate to the present invention, are indicated by references 74, 76, 78 and 80, respectively, are referred to as a power ON/OFF switch (SW1) for the video-signal processing unit 12, a lamp ON/OFF switch (SW2) for the lamp 18, a mode-selection switch (SW3) for selecting an operation mode in the video-signal processing unit 12, and a white-balance-adjustment initiation switch (SW4) for initiating a readjustment of the color correction factors for the white-balance correction.

By operating the mode-selection switch (SW3) 78, an operation mode is switched from a usual operation mode to a white-balance-adjustment operation mode and vice versa in the video-signal processing unit 12. Of course, when the power ON/OFF switch (SW1) 74 is turned ON, the usual operation mode is selected, and the usual operation mode is switched to the white-balance-adjustment operation mode by once operating the mode-selection switch (SW3) 78. When the mode-selection switch (SW3) 78 is further operated, the white-balance-adjustment operation mode is switched to the usual operation mode. Namely, when the mode-selection switch (SW3) 78 is operated every time, one of the two modes is switched to the other mode.

Also, whenever the mode-selection switch (SW3) 78 is operated, the switching circuit 66 is operated so as to switch the connection of the histogram-generating circuit 64 to either the frame memory 36 or the video-process circuit 38. Namely, when the usual mode is selected, the histogram-generating circuit 64 is connected to the video-process circuit 38, and, when the white-balance-adjustment operation mode is selected, the histogram-generating circuit 64 is connected to the frame memory 36.

Figure 5:
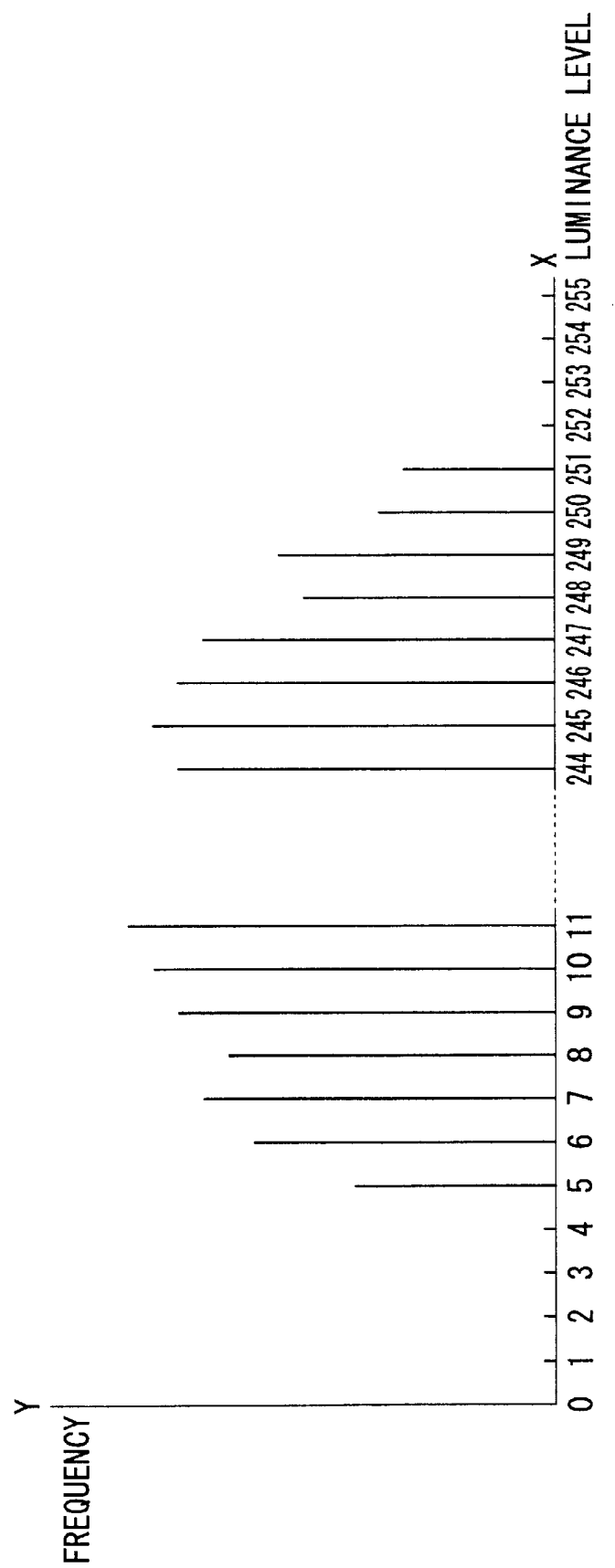
FIG. 5 is a graph showing a histogram, by way of example, generated in a histogram generating circuit of the electronic endoscope of FIG. 1 on the basis of a frame or field of luminance signals.

FIG. 5 shows a histogram, by way of example, which is generated, in the histogram-generating circuit 64, on the basis of a frame or field of luminance signals obtained from the video-process circuit 38. In this histogram, the abscissa (X) represents a distribution of luminance levels of all of the luminance signals included in one frame or field, and the ordinate (Y) represents a frequency or number of luminance signals exhibiting a same luminance level.

In this embodiment, as is apparent from FIG. 5, the luminance-signals included in one frame or field are sorted by 256 luminance levels which define a full histogram-definition range ($0 \leq X \leq 255$). A luminance level "0" represents a minimum luminance level-value corresponding to a pedestal level-value of the video signal produced in the video-process circuit 38, and a luminance level of "255" represents a maximum luminance level-value.

Note, in the example of the histogram shown in FIG. 5, there is no luminance signal falling in a lowest-luminance-level range defined by the luminance levels "0" and "4", and there is no luminance signal falling in a highest-luminance-level range defined by the luminance levels "252" and "255".

Figure 6:
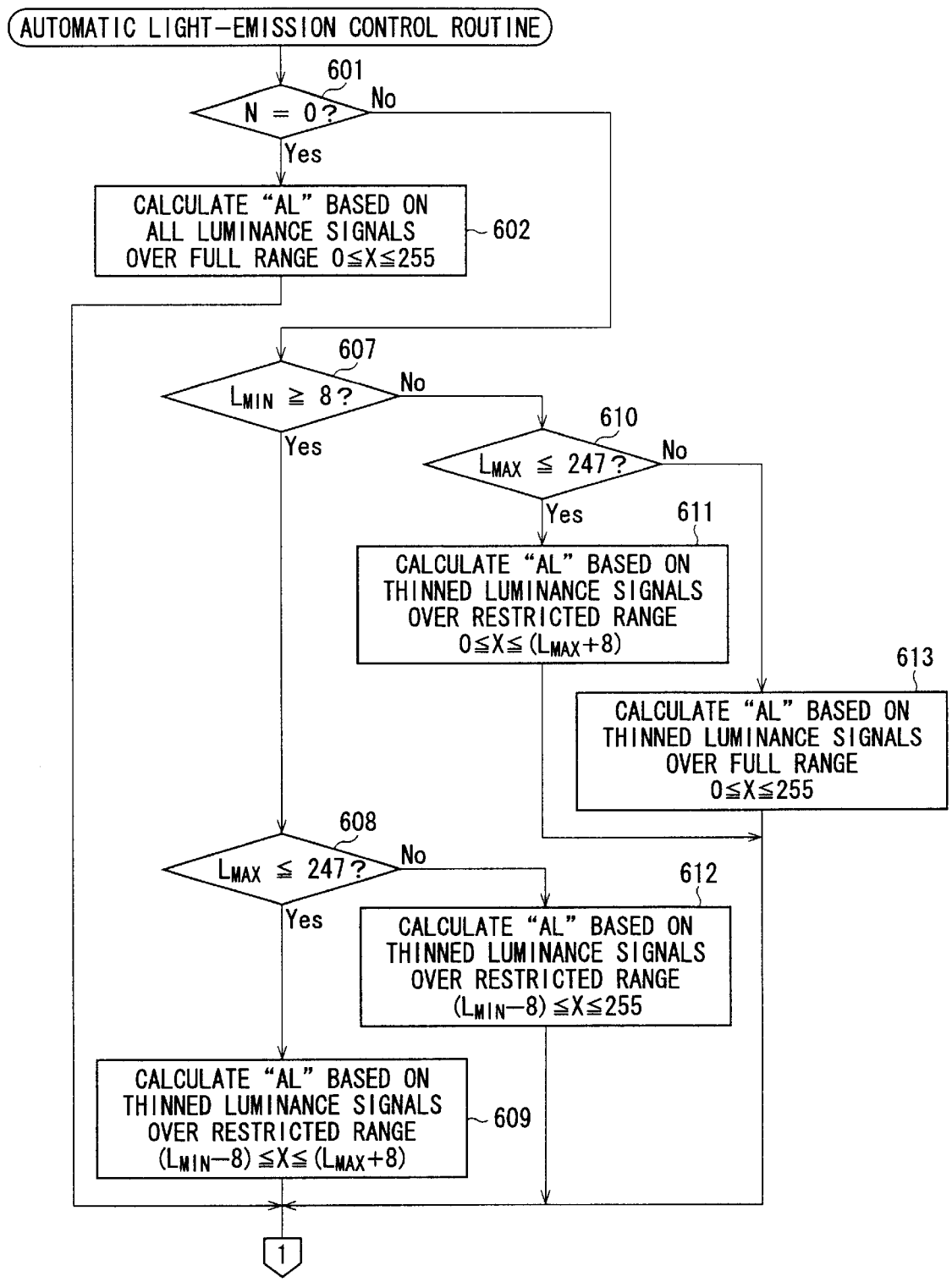
FIG. 6 is a part of a flowchart of an automatic light-emission control routine executed in a system control circuit of the electronic endoscope of FIG. 1.
Figure 7:
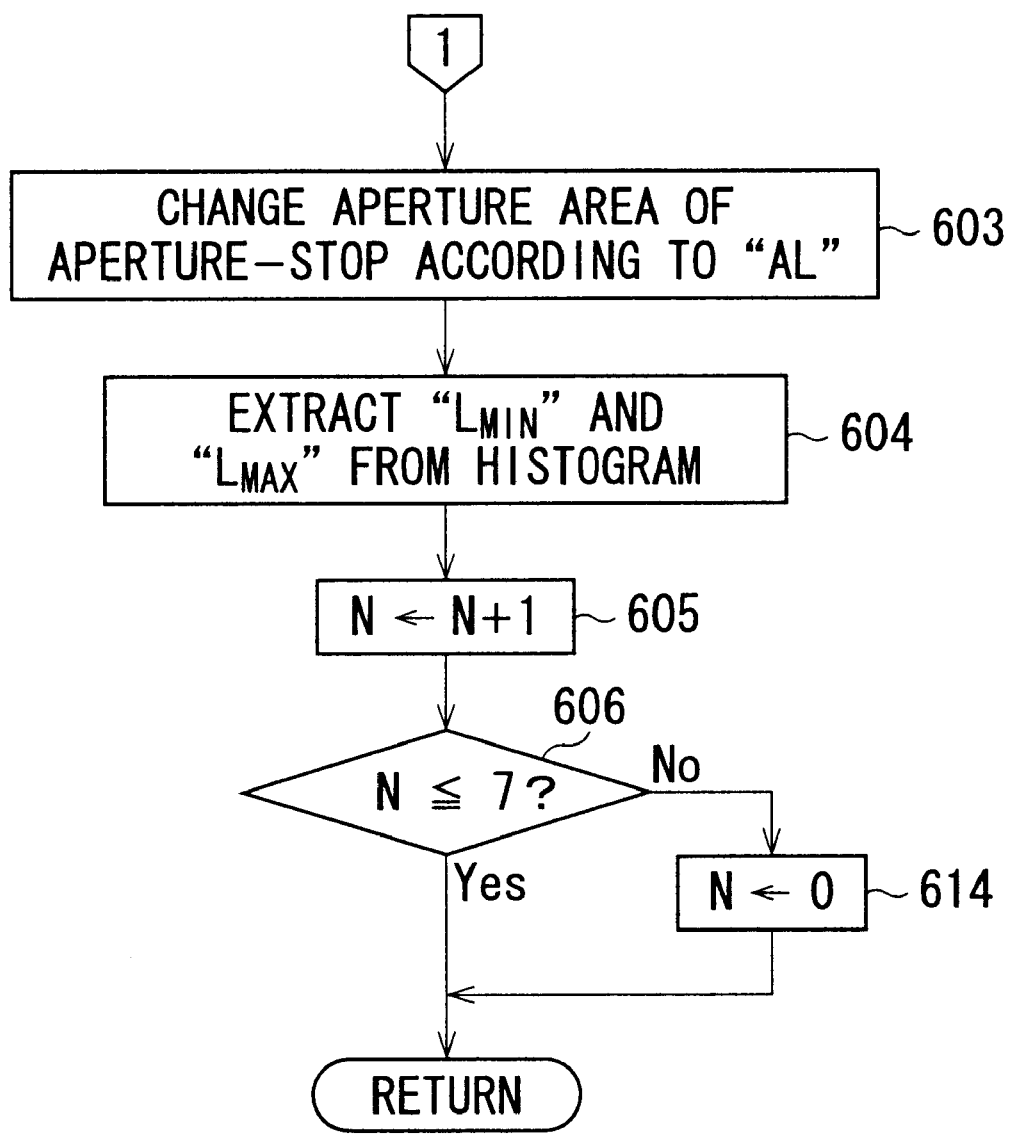
FIG. 7 is a remaining part of the flowchart of the automatic light-emission control routine referred to in FIG. 6.

FIGS. 6 and 7 show a flowchart of an automatic light-emission control routine executed by the system control circuit 30. This automatic light-emission control routine is constituted as a time-interruption routine, and this time-interruption routine is repeatedly executed at a regular time-interval which is predetermined in accordance with a used image-reproduction method, such as the NTSC system, the PAL system or the like. For example, when the PAL system is used, the execution of the time-interruption routine is repeated at a regular time-interval of 1/25 sec, and, when the NTSC system is used, the execution of the time-interruption routine is repeated at a regular time-interval of 1/30 sec. Note, an execution of this time-interruption routine is started by turning the power ON/OFF switch (SW1) 74 ON.

At step 601, it is determined whether a count number of a counter N is equal to "1". If N=0, the control proceeds to step 602, in which an average luminance level-value AL is exactly calculated on the basis of a first histogram generated in the histogram-generating circuit 64. Namely, an exact calculation of the average luminance level-value AL is carried out as follows:

$$AL = \frac{\sum_{n=0}^{n=255} L_n * S_n}{TP}$$

$$TP = \sum_{n=0}^{n=255} S_n$$

Herein:
$L_n$ is a luminance level-value corresponding to a luminance level n;
$S_n$ is a number (frequency) of luminance signals exhibiting the luminance level n; and
TP is a total number of luminance signals included in the first histogram.

As is apparent from the above formula, at step 602, the exact calculation of the average luminance level-value AL is carried out over the full histogram-definition range ($0 \leq X \leq 255$), and is thus based on all of the luminance signals included in the first histogram. Accordingly, the calculated result AL is reliable.

At step 603, an aperture area of the aperture-stop 20 is changed in accordance with the exactly-calculated average luminance level-value AL. Namely, the motor 58 is driven by operating the driver circuit 60 under control of the system control circuit 30, such that a setting of an aperture area, which corresponds to the exactly-calculated average luminance level-value AL, is given to the aperture-stop 20, enabling the radiation of the illuminating-light from the distal end of the flexible scope 10 to be properly regulated, whereby a constant overall brightness of a reproduced object image on the monitor 40 is maintained.

Figure 8:
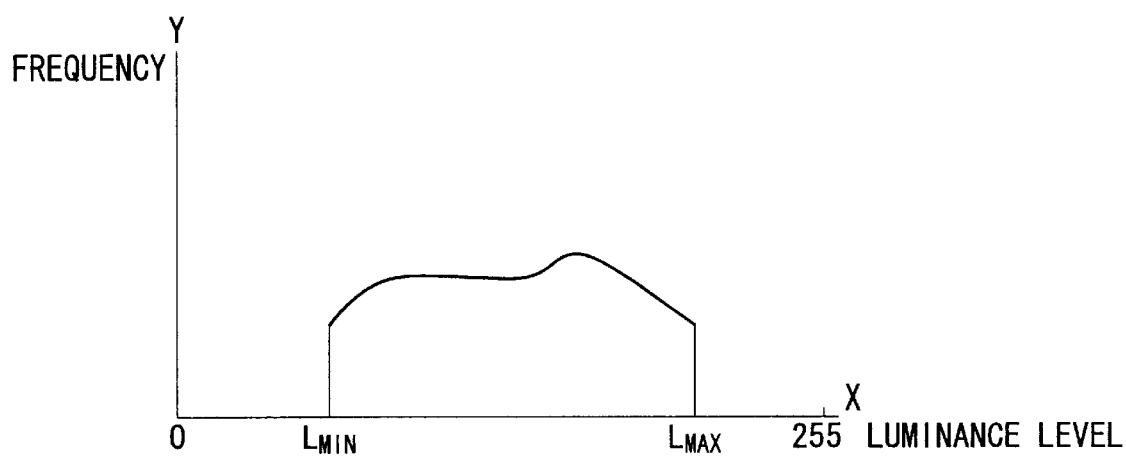
FIG. 8 is a graph showing one type of histogram, by way of example, generated in the histogram-generating circuit, for explanation of the automatic light-emission control routine shown in FIGS. 6 and 7.

At step 604, a minimum luminance level $L_{MIN}$ and a maximum luminance level $L_{MAX}$ are extracted from the first histogram generated in the histogram-generating circuit 64, and are temporarily stored in the RAM of the system control circuit 30. Referring to FIG. 8, the first histogram is shown by way of example. Of course, in this example, the first histogram includes no luminance signal exhibiting a luminance level less than the minimum luminance level $L_{MIN}$, and no luminance signal exhibiting a luminance level more than the maximum luminance level $L_{MAX}$.

At step 605, the count number of the counter N is incremented by "1". Then, at step 606, it is determined whether the count number of the counter N has reached "7". At this stage, since N=1, the routine once ends.

Figure 9:
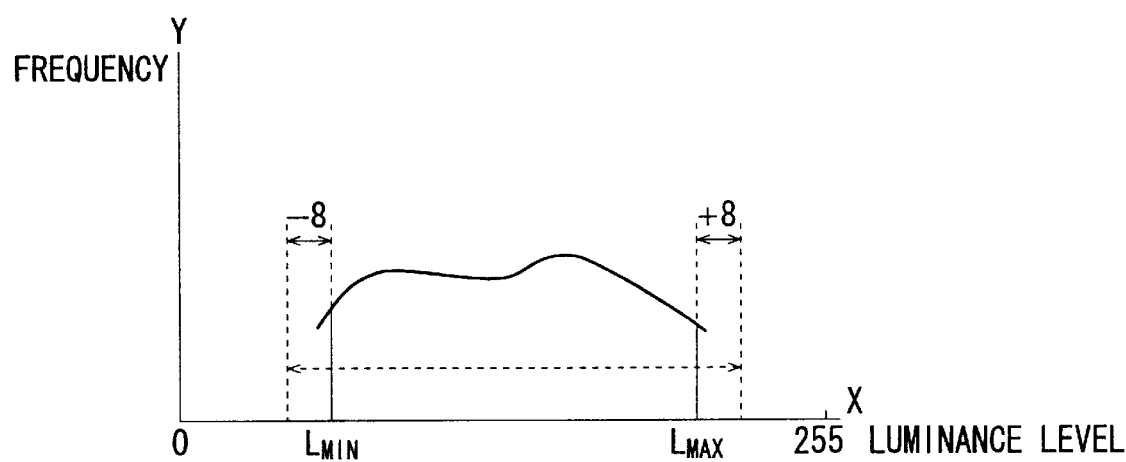
FIG. 9 is a graph showing a histogram, exhibiting a close resemblance to that of FIG. 8, for explanation of the automatic light-emission control routine shown in FIGS. 6 and 7.

After the given time (1/30 sec or 1/25 sec) has elapsed, the routine is again executed. In this second execution of the routine, the first histogram is renewed with a second histogram in the histogram-generating circuit 64. Referring to FIG. 9, the second histogram is shown by way of example. In general, two histograms, which are consecutively generated in the histogram-generating circuit 64, exhibit a close resemblance to each other, as is apparent from a comparison of both the histograms of FIGS. 8 and 9. The resemblance is especially apparent, for example, when the distal end of the flexible scope 10 is not almost moved to carefully observe a medical image of a patient, in this case, the two consecutive histograms may be essentially identical to each other.

In the second execution of the routine after the elapsed time (1/30 sec or 1/25 sec), since N=1, the control proceeds from step 601 to step 607, in which it is determined whether the minimum luminance level $L_{MIN}$ is greater than a threshold luminance level "8". If $L_{MIN} \geq 8$, the control proceeds to step 608, in which it is determined whether the maximum luminance level $L_{MAX}$ is less than a threshold luminance level "247". If $L_{MAX} \leq 247$, the control proceeds to step 609. Note, both the threshold luminance levels "8" and "247" may be suitably determined as discussed hereinafter.

At step 609, an average luminance level-value AL is approximately calculated on the basis of the second histogram generated in the histogram-generating circuit 64. Namely, the approximate calculation of the average luminance level-value AL is carried out as follows:

$$AL = \frac{\sum_{n=i}^{n=j} L_{2n} * S_{2n}}{\sum_{n=i}^{n=j} S_{2n}}$$

$$i = \left\lceil \frac{L_{MIN} - 8}{2} \right\rceil$$

$$j = \left\lceil \frac{L_{MAX} + 8}{2} \right\rceil$$

Herein:

$L_{2n}$ is a luminance level-value corresponding to a luminance level "2n";

$S_{2n}$ is a number (frequency) of luminance signals exhibiting the even-numbered luminance level "2n"; and

[X] is a gaussian symbol which represents an integer art of a calculated result X.

As is apparent from the above formula, at step 609, the approximate calculation of the average luminance level-value AL is carried out over a restricted range of the full histogram-definition range ($0 \leq X \leq 255$), defined by a double-headed arrow in FIG. 9, and is based on only a part ($S_{2n}$) of the luminance signals included in the second histogram.

In particular, as shown in FIG. 9, the restricted range of the full histogram-definition range ($0 \leq X \leq 255$) is defined as follows:

$$(L_{MIN} - 8) \leq X \leq (L_{MAX} + 8)$$

Namely, the restricted range $(L_{MIN}-8) \leq X \leq (L_{MAX}+8)$ is obtained by somewhat extending the first histogram range defined by the minimum luminance level $L_{MIN}$ and the maximum luminance level $L_{MAX}$ thereof. If the first and second histograms (FIGS. 8 and 9) exhibit a close resemblance to each other, the second histogram may completely fall in the restricted range as defined above, due to the close resemblance between the first and second histograms. In this embodiment, a degree of extension of the first histogram range at each limit end thereof corresponds to a range section including eight consecutive luminance levels, which is about 3% of the full histogram-definition range ($0 \leq X \leq 255$). Note, the degree of the extension of the first histogram range at each limit end thereof may be from about 3% to about 5% of the full histogram-definition range ($0 \leq X \leq 255$).

Also, as mentioned above, the approximate calculation of the average luminance level-value AL is based on only a part of the luminance signals included in the second histogram. Namely, in this approximate calculation, only the luminance signals ($S_{2n}$) included in the thinned or even-numbered luminance levels ("2n") of the second histogram are taken into account, but remaining luminance signals included in the odd-numbered luminance levels ($S_{2n-1}$) of the second histogram are neglected in the calculation.

Thus, at step 609, the approximate calculation of the average luminance level-value AL can be quickly finished, because the approximate calculation of the average luminance level-value AL is carried out over the restricted range $(L_{MIN}-8) \leq X \leq (L_{MAX}+8)$ of the full histogram-definition range ($0 \leq X \leq 255$), and is based on only the luminance signals included in the thinned luminance levels ("2n") of the second histogram. Nevertheless, the approximately-calculated result AL is reliable as long as a movement of the distal end of the flexible scope 10 is small, due to the required resemblance between the two consecutive histograms or first and second histograms (FIGS. 8 and 9).

After the approximate calculation of the average luminance level-value AL is finished at step 609, the control proceeds from step 609 to step 603, in which an aperture area of the aperture-stop 20 is changed in accordance with the approximately-calculated average luminance level-value AL, such that the radiation of the illuminating-light from the distal end of the flexible scope 10 is properly regulated, whereby a constant overall brightness of a reproduced object image on the monitor 40 is maintainable.

At step 604, a minimum luminance level $L_{MIN}$ and a maximum luminance level $L_{MAX}$ are extracted from the second histogram generated in the histogram-generating circuit 64, and are temporarily stored in the RAM of the system control circuit 30.

At step 605, the count number of the counter N is incremented by "1". Then, at step 606, it is determined whether the count number of the counter N has reached "7". At this stage, since N=2, the routine once ends.

In the second execution of the routine, at step 607, if the minimum luminance level $L_{MIN}$ is less than the threshold luminance level "8", the control proceeds from step 607 to step 610, in which it is determined whether the maximum luminance level $L_{MAX}$ is less than the threshold luminance level "247". If $L_{MAX} \leq 247$, the control proceeds from step 610 to step 611.

Figure 10:
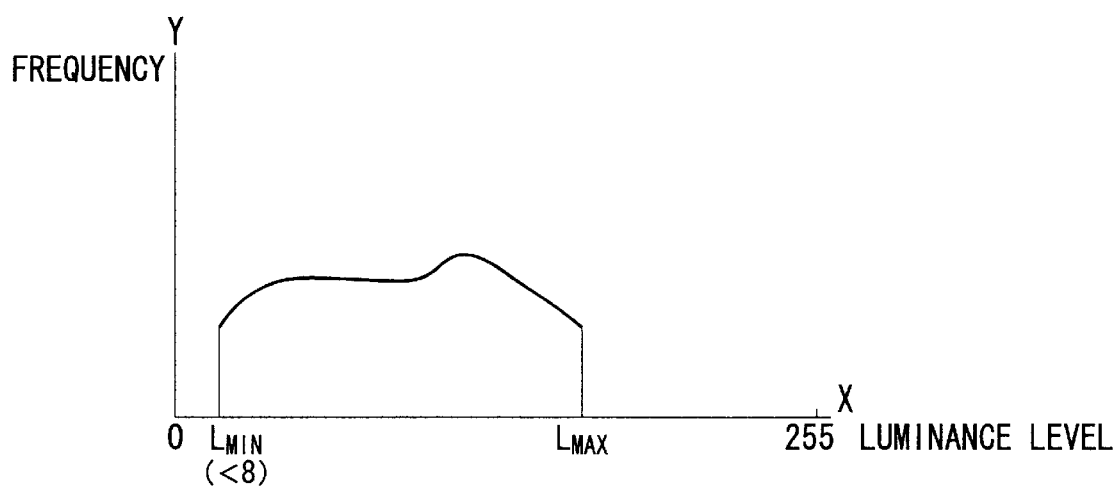
FIG. 10 is a graph showing another type of histogram, by way of example, generated in the histogram-generating circuit, for explanation of the automatic light-emission control routine shown in FIGS. 6 and 7.
Figure 11:
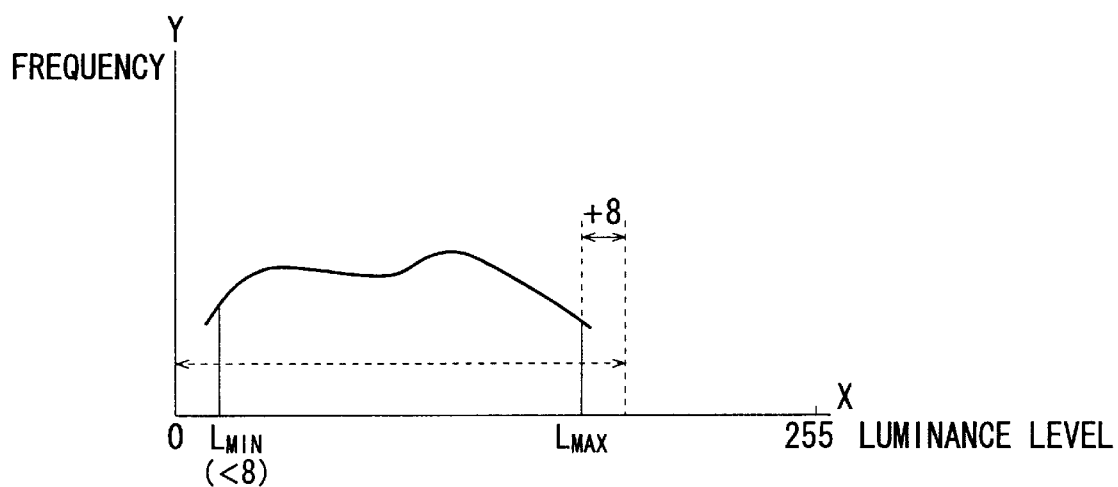
FIG. 11 is a graph showing a histogram, exhibiting a close resemblance to that of FIG. 10, for explanation of the automatic light-emission control routine shown in FIGS. 6 and 7.

If $L_{MIN} < 8$ and $L_{MAX} \leq 247$, the first histogram must be, for example, as shown in FIG. 10, and the second histogram must exhibit a close resemblance to that of FIG. 10, as shown in FIG. 11. In this case, of course, the aperture area of the aperture-stop 20 has been changed in accordance with an average luminance level AL exactly calculated on the basis of the first histogram of FIG. 10 (step 602), and the minimum and maximum luminance levels $L_{MIN}$ and $L_{MAX}$ of the first histogram (FIG. 10) have been stored in the RAM of the system control circuit 30 (step 604).

At step 611, an average luminance level-value AL is approximately calculated on the basis of the second histogram (FIG. 11) generated in the histogram-generating circuit 64. Namely, the approximate calculation of the average luminance level-value AL is carried out as follows:

$$AL = \frac{\sum_{n=0}^{n=j} L_{2n} * S_{2n}}{\sum_{n=0}^{n=j} S_{2n}}$$

$$j = \left\lceil \frac{L_{MAX} + 8}{2} \right\rceil$$

As is apparent from the above formula, at step 611, the approximate calculation of the average luminance level-value AL is carried out over a restricted range of the full histogram-definition range ($0 \leq X \leq 255$), defined by a double-headed arrow in FIG. 11, and is based on only a part ($S_{2n}$) of the luminance signals included in the second histogram (FIG. 11).

In particular, as shown in FIG. 11, the restricted range of the full histogram-definition range ($0 \leq X \leq 255$) is defined as follows:

$0 \leq X \leq (L_{MAX}+8)$

Namely, when the minimum luminance level $L_{MIN}$ of the first histogram (FIG. 10) is less than threshold luminance level "8", the lowest limit end of the restricted range $0 \leq X \leq (L_{MAX}+8)$ is defined by extending the minimum luminance level $L_{MIN}$ of the first histogram (FIG. 10) to the luminance level "0". Of course, if the first and second histograms (FIGS. 10 and 11) exhibit a close resemblance to each other, the second histogram (11) may completely fall in the restricted range $0 \leq X \leq (L_{MAX}+8)$ as defined above, due to the close resemblance between the first and second histograms (FIGS. 10 and 11).

Also, the approximate calculation of the average luminance level-value AL at step 611 is based on only the part of the luminance signals included in the second histogram (FIG. 11). Namely, in this approximate calculation, only the luminance signals ($S_{2n}$) included in the thinned or even-numbered luminance levels ("2n") of the second histogram (FIG. 11) are taken into account, but the remaining luminance signals included in the odd-numbered luminance levels ($S_{2n-1}$) of the second histogram (FIG. 11) are neglected in the calculation.

Thus, at step 611, the approximate calculation of the average luminance level-value AL can be quickly finished, because the approximate calculation of the average luminance level-value AL is carried out over the restricted range $0 \leq X \leq (L_{MAX}+8)$ of the full histogram-definition range ($0 \leq X \leq 255$), and is based on only the luminance signals included in the thinned luminance levels ("2n") of the second histogram (FIG. 11). Nevertheless, the approximately calculated result AL is reliable as long as the movement of the distal end of the flexible scope 10 is small, due to the required resemblance between the two consecutive histograms or first and second histograms (FIGS. 10 and 11).

Of course, after the approximate calculation of the average luminance level-value AL is finished at step 611, the control proceeds from step 611 to step 603, in which an aperture area of the aperture-stop 20 is changed in accordance with the approximately-calculated average luminance level-value AL (step 611). Also, at step 604, a minimum luminance level $L_{MIN}$ and a maximum luminance level $L_{MAX}$ are extracted from the second histogram (FIG. 11) generated in the histogram-generating circuit 64, and are temporarily stored in the RAM of the system control circuit 30. Further, at step 605, the count number of the counter N is incremented by "1". Then, at step 606, it is determined whether the count number of the counter N has reached "7". At this stage, since N=2, the routine once ends.

In the second execution of the routine, at step 608, if the maximum luminance level $L_{MAX}$ is greater than the threshold luminance level "247", the control proceeds from step 608 to step 612.

Figure 12:
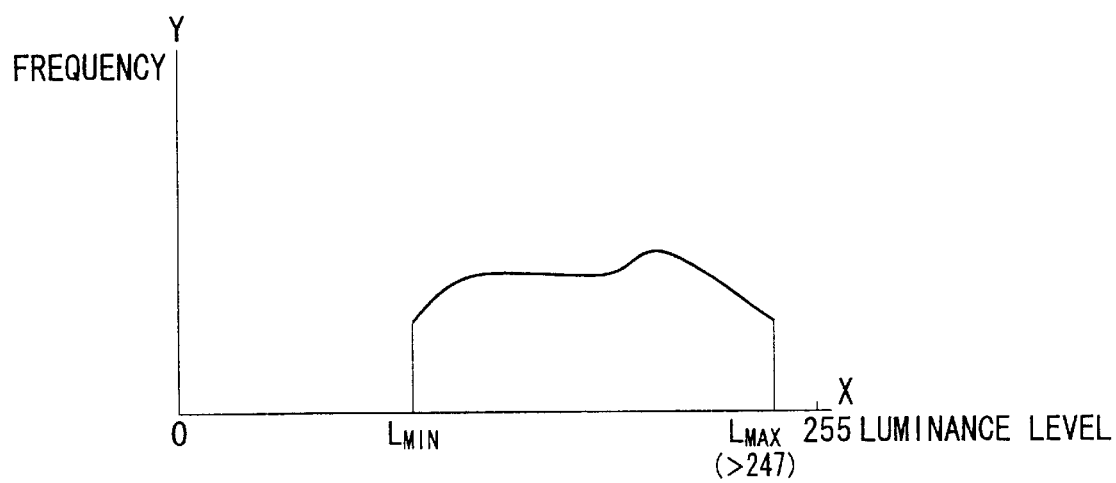
FIG. 12 is a graph showing yet another type of histogram, by way of example, generated in the histogram-generating circuit, for explanation of the automatic light-emission control routine shown in FIGS. 6 and 7.
Figure 13:
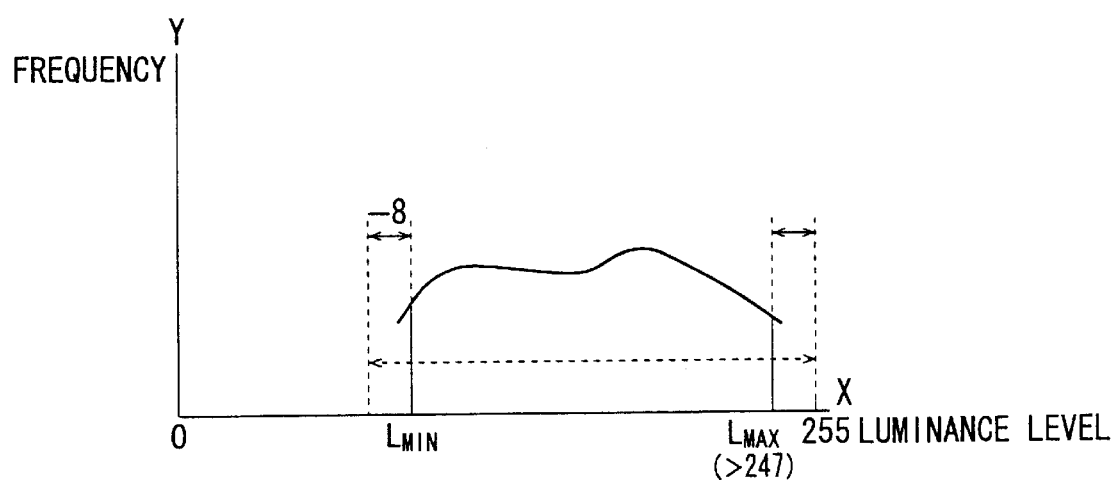
FIG. 13 is a graph showing a histogram, exhibiting a close resemblance to that of FIG. 12, for explanation of the automatic light-emission control routine shown in FIGS. 6 and 7.

If $L_{MIN} \geq 8$ and $L_{MAX} > 247$, the first histogram must be, for example, as shown in FIG. 12, and the second histogram must exhibit a close resemblance to that of FIG. 12, as shown in FIG. 13. In this case, of course, the aperture area of the aperture-stop 20 has been changed in accordance with an average luminance level AL exactly calculated on the basis of the first histogram of FIG. 12 (step 602), and the maximum and maximum luminance levels $L_{MIN}$ and $L_{MAX}$ of the first histogram (FIG. 12) have been stored in the RAM of the system control circuit 30 (step 604).

At step 612, an average luminance level-value AL is approximately calculated on the basis of the second histogram (FIG. 13) generated in the histogram-generating circuit 64. Namely, the approximate calculation of the average luminance level-value AL is carried out as follows:

$$AL = \frac{\sum_{n=0}^{n=i} L_{2n} * S_{2n}}{\sum_{n=0}^{n=i} S_{2n}}$$

$$i = \left\lceil \frac{L_{MIN} - 8}{2} \right\rceil$$

As is apparent from the above formula, at step 612, the approximate calculation of the average luminance level-value AL is carried out over a restricted range of the full histogram-definition range ($0 \leq X \leq 255$), defined by a double-headed arrow in FIG. 13, and is based on only a part ($S_{2n}$) of the luminance signals included in the second histogram (FIG. 13).

In particular, as shown in FIG. 13, the restricted range of the full histogram-definition range ($0 \leq X \leq 255$) is defined as follows:

$$(L_{MIN} - 8) \leq X \leq 255$$

Namely, when the maximum luminance level $L_{MAX}$ of the first histogram (FIG. 12) is greater than the threshold luminance level "247", the highest limit end of the restricted range ($L_{MIN} - 8) \leq X \leq 255$ is defined by extending the maximum luminance level $L_{MAX}$ of the first histogram (FIG. 12) to the luminance level "247". Of course, if the first and second histograms (FIGS. 12 and 13) exhibit a close resemblance to each other, the second histogram (13) may completely fall in the restricted range ($L_{MIN} - 8) \leq X \leq 255$ as defined above, due to the close resemblance between the first and second histograms (FIGS. 12 and 13).

Also, the approximate calculation of the average luminance level-value AL at step 612 is based on only the part of the luminance signals included in the second histogram (FIG. 13). Namely, in this approximate calculation, only the luminance signals ($S_{2n}$) included in the thinned or even-numbered luminance levels ("2n") of the second histogram (FIG. 13) are taken into account, but the remaining luminance signals included in the odd-numbered luminance levels ($S_{2n-1}$) of the second histogram (FIG. 13) are neglected in the calculation.

Thus, at step 612, the approximate calculation of the average luminance level-value AL can be quickly completed, because the approximate calculation of the average luminance level-value AL is carried out over the restricted range ($L_{MIN} - 8) \leq X \leq 255$ of the full histogram-definition range ($0 \leq X \leq 255$), and is based on only the luminance signals included in the thinned luminance levels ("2n") of the second histogram (FIG. 13). Nevertheless, the approximately-calculated result AL is reliable as long as the movement of the distal end of the flexible scope 10 is small, due to the required resemblance between the two consecutive histograms or first and second histograms (FIGS. 12 and 13).

Of course, after the approximate calculation of the average luminance level-value AL is finished at step 612, the control proceeds from step 612 to step 603, in which an aperture area of the aperture-stop 20 is changed in accordance with the approximately-calculated average luminance level-value AL (step 612). Also, at step 604, a minimum luminance level $L_{MIN}$ and a maximum luminance level $L_{MAX}$ are extracted from the second histogram (FIG. 13) generated in the histogram-generating circuit 64, and are temporarily stored in the RAM of the system control circuit 30. Further, at step 605, the count number of the counter N is incremented by "1". Then, at step 606, it is determined whether the count number of the counter N has reached "7". At this stage, since N=2, the routine once ends.

In the second execution of the routine, at step 610, if the maximum luminance level $L_{MAX}$ is greater than the threshold luminance level "247", the control proceeds from step 610 to step 613.

Figure 14:
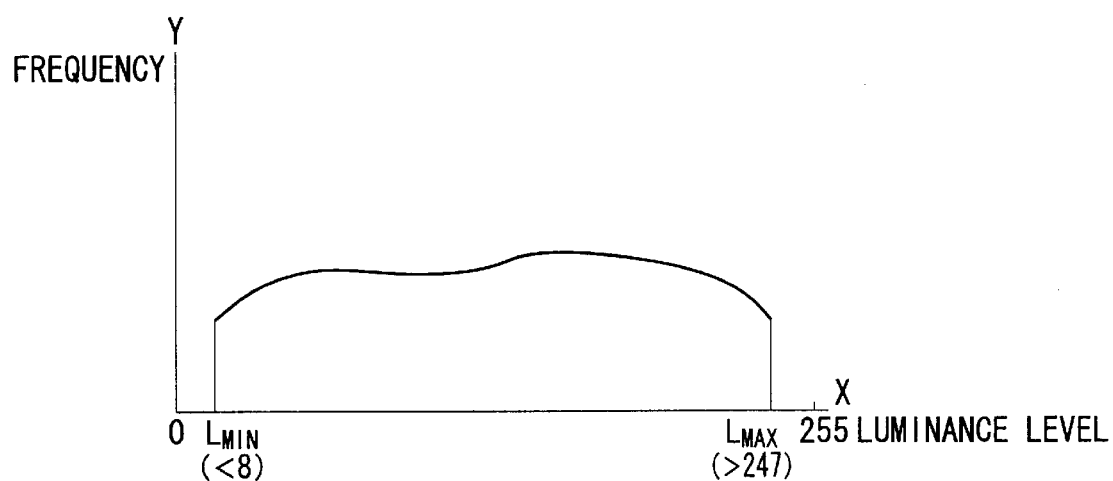
FIG. 14 is a graph showing still yet another type of histogram, by way of example, generated in the histogram-generating circuit, for explanation of the automatic light-emission control routine shown in FIGS. 6 and 7.
Figure 15:
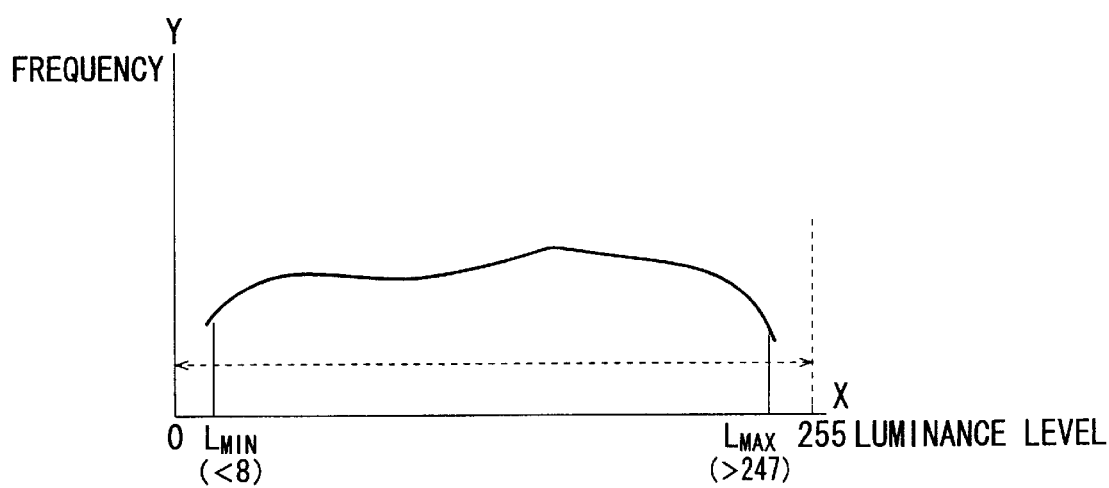
FIG. 15 is a graph showing a histogram, exhibiting a close resemblance to that of FIG. 14, for explanation of the automatic light-emission control routine shown in FIGS. 6 and 7.

If $L_{MIN} < 8$ and $L_{MAX} > 247$, the first histogram must be, for example, as shown in FIG. 14, and the second histogram must exhibit a close resemblance to that of FIG. 14, as shown in FIG. 15. In this case, of course, the aperture area of the aperture-stop 20 has been changed in accordance with an average luminance level AL exactly calculated on the basis of the first histogram of FIG. 14 (step 602), and the minimum and maximum luminance levels $L_{MIN}$ and $L_{MAX}$ of the first histogram (FIG. 14) have been stored in the RAM of the system control circuit 30 (step 604).

At step 613, an average luminance level-value AL is approximately calculated on the basis of the second histogram (FIG. 15) generated in the histogram-generating circuit 64. Namely, the approximate calculation of the average luminance level-value AL is carried out as follows:

$$AL = \frac{\sum_{n=0}^{n=127} L_{2n} * S_{2n}}{\sum_{n=0}^{n=127} S_{2n}}$$

As is apparent from the above formula, at step 613, the approximate calculation of the average luminance level-value AL is carried out over the full histogram-definition range ($0 \leq X \leq 255$), shown by a double-headed arrow in FIG. 15, and is based on only a part ($S_{2n}$) of the luminance signals included in the second histogram (FIG. 15).

When $L_{MIN} < 8$ and $l_{MAX} > 247$, the range, defined by the minimum and maximum luminance levels $L_{MIN}$ and $L_{MAX}$ of the first histogram (FIG. 14), is extended to the full histogram-definition range ($0 \leq X \leq 255$). Thus, the approximate calculation of the average luminance AL at step 613 is carried out over the full histogram-definition range ($0 \leq X \leq 255$), but is based on only the part of the luminance signals included in the second histogram (FIG. 15). Namely, in this approximate calculation, only the luminance signals ($S_{2n}$) included in the thinned or even-numbered luminance levels ("2n") of the second histogram (FIG. 15) are taken into account, but the remaining luminance signals included in the odd-numbered luminance levels ($S_{2n-1}$) of the second histogram (FIG. 15) are neglected in the calculation.

Accordingly, at step 613, the approximate calculation of the average luminance level-value AL can be quickly completed. Nevertheless, the approximately-calculated result AL is reliable as long as the movement of the distal end of the flexible scope 10 is small, due to the required resemblance between the two consecutive histograms or first and second histograms (FIGS. 14 and 15).

Of course, after the approximate calculation of the average luminance level-value AL is finished at step 613, the control proceeds from step 613 to step 603, in which an aperture area of the aperture-stop 20 is changed in accordance with the approximately-calculated average luminance level-value AL (step 613). Also, at step 604, a minimum luminance level $L_{MIN}$ and a maximum luminance level $L_{MAX}$ are extracted from the second histogram (FIG. 15) generated in the histogram-generating circuit 64, and are temporarily stored in the RAM of the system control circuit 30. Further, at step 605, the count number of the counter N is incremented by "1". Then, at step 606, it is determined whether the count number of the counter N has reached "7". At this stage, since N=2, the routine once ends.

Thereafter, although the routine is repeatedly executed at the regular interval of the given time (1/30 sec or 1/25 sec), an average luminance level AL is merely calculated at one of steps 609, 611, 612 and 613 in substantially the same manner as mentioned above, and an aperture area of the aperture-stop 20 is changed in accordance with the approximately-calculated average luminance level AL, until the count number of the counter N reaches "7" at step 606.

At step 606, when the count number of the counter N reaches "8", the control proceeds from 606 to 614, in which the counter N is reset to "0". Of course, when the routine is executed after the counter N has been reset, the control proceeds from step 601 to step 602 (N=0), in which an exact and reliable calculation of an average luminance level-value AL is carried out over a full histogram-definition range ($0 \leq X \leq 255$), and which is based on all luminance signals included in a histogram generated in the histogram-generating circuit 64.

Namely, in this embodiment, after an approximate calculation of an average luminance level AL is repeated seven times, an exact and reliable calculation of an average luminance level AL is carried out. Accordingly, when the distal end of the flexible scope 10 is moved more than a small amount during the repetition of the approximate calculation of the average luminance level AL, a brightness of a reproduced image on the monitor 40 may become irregular. Nevertheless, the brightness of the reproduced image on the monitor 40 can be almost immediately returned to a proper constant brightness level, due to the exact and reliable calculation of the average luminance level AL being necessarily carried out after the approximate calculation of the average luminance level AL has been repeated seven times.

Figure 16:
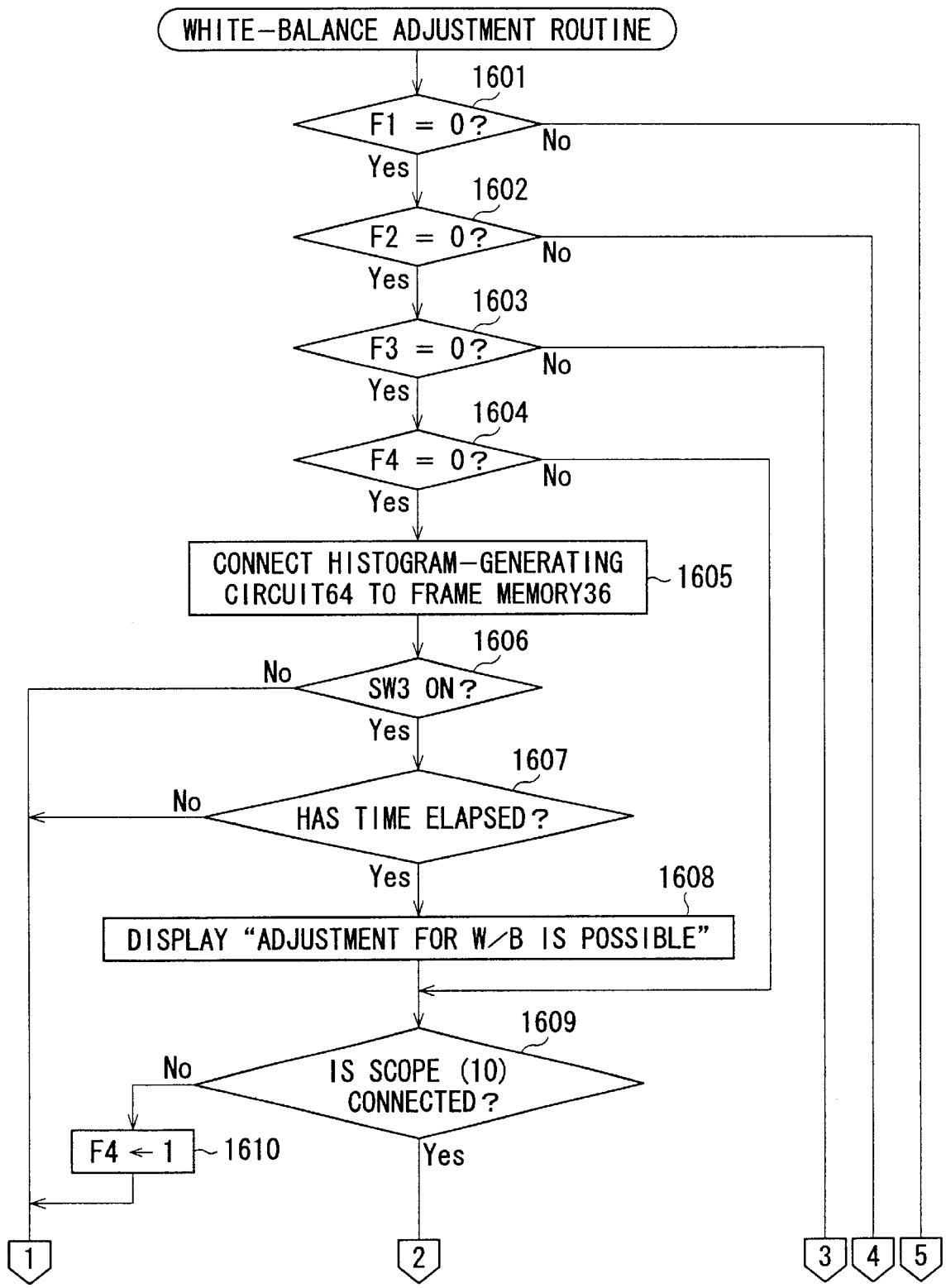
FIG. 16 is a part of a flowchart of a white-balance adjustment routine executed in a system control circuit of the electronic endoscope of FIG. 1.
Figure 17:
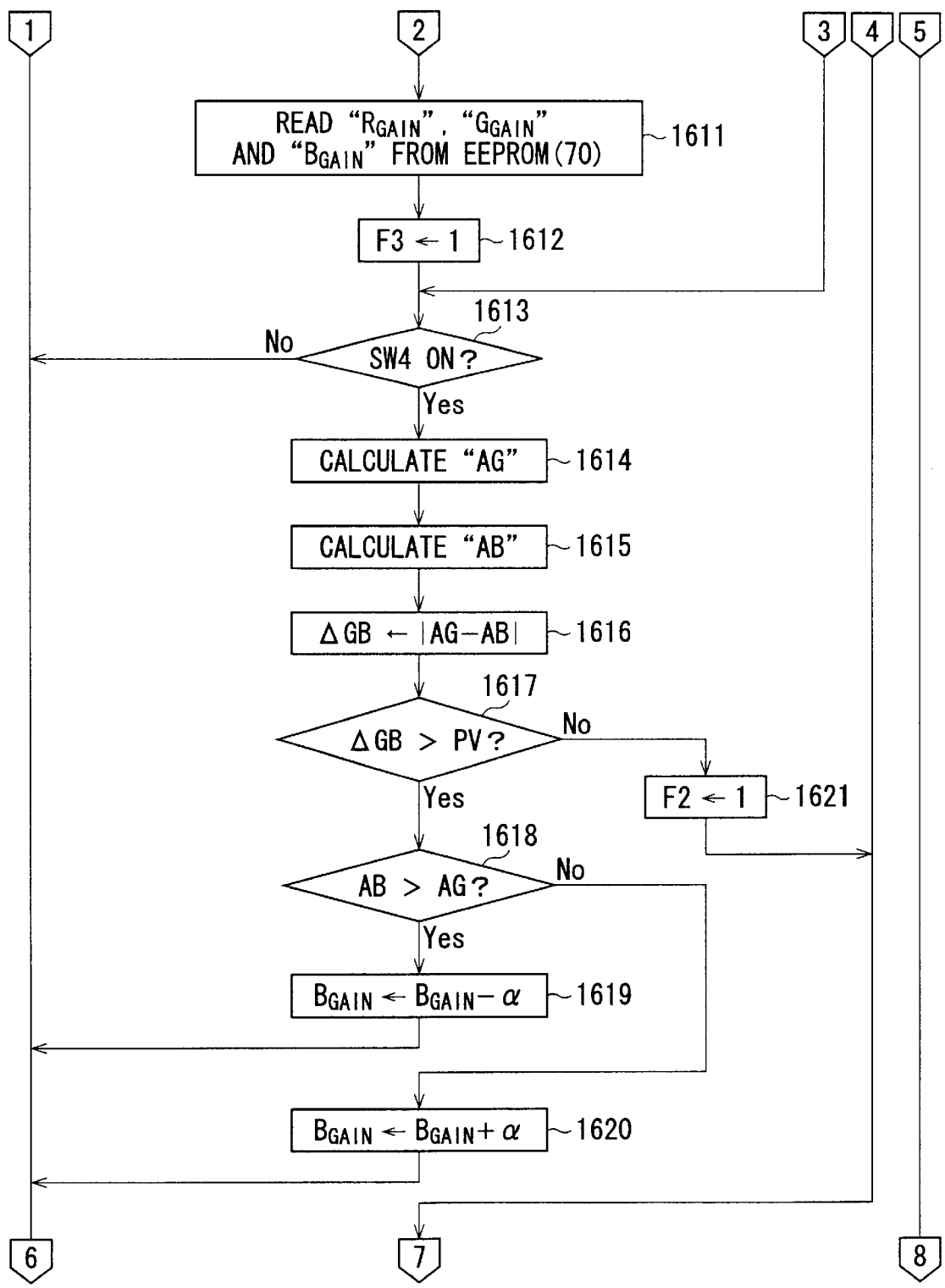
FIG. 17 is another part of the flowchart of the white-balance adjustment routine referred to in FIG. 16.
Figure 18:
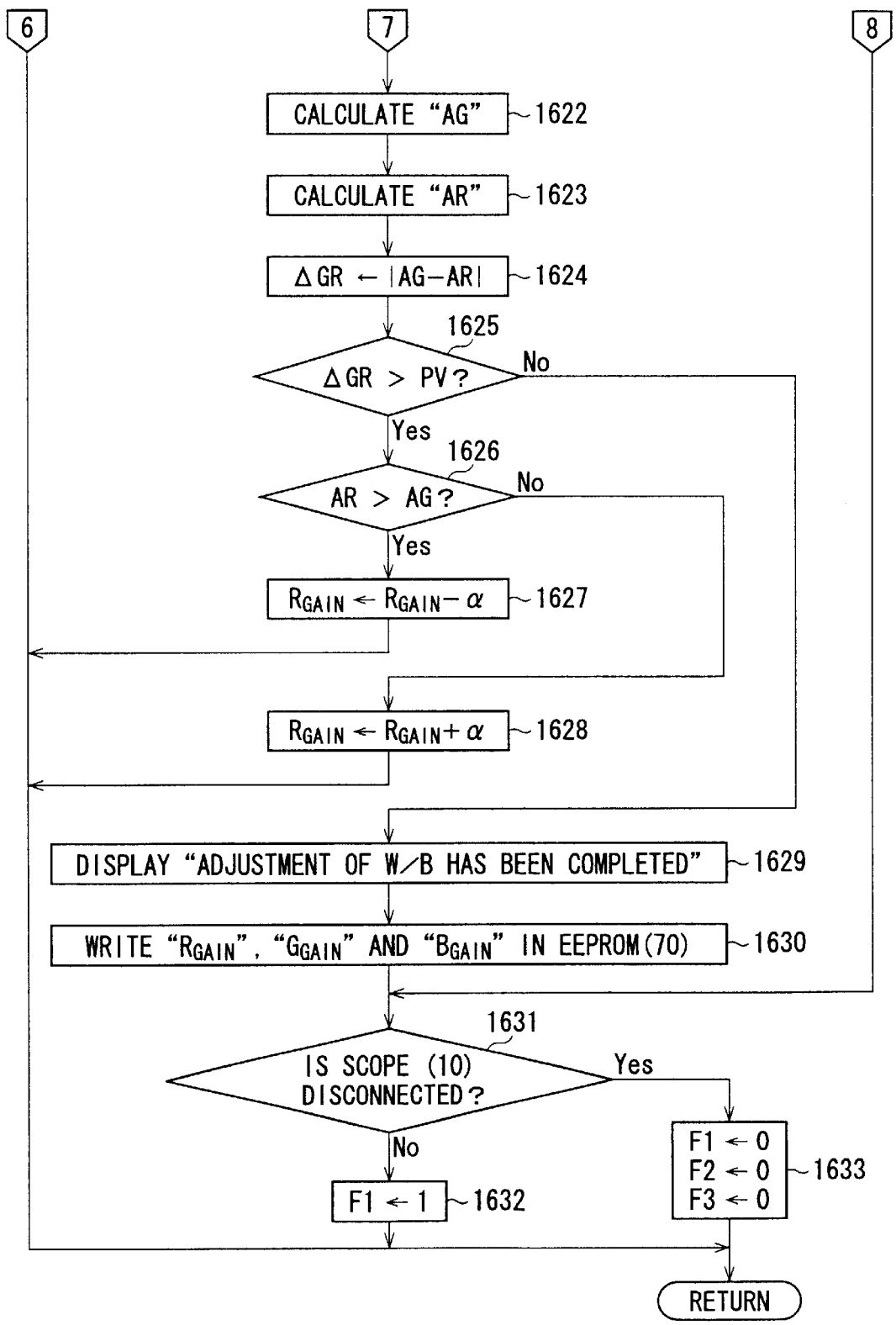
FIG. 18 is a remaining part of the flowchart of the white-balance adjustment routine referred to in FIG. 16.

FIGS. 16, 17 and 18 show a flowchart of a white-balance adjustment routine executed by the system control circuit 30. This white-balance adjustment routine is also constituted as a time-interruption routine, and this time-interruption routine is repeatedly executed at a regular time-interval, which is predetermined in accordance with a used image-reproduction method, such as the NTSC system, the PAL system or the like. For example, when the PAL system is used, an execution of the time-interruption routine is repeated at a regular time-interval of 1/25 sec, and, when the NTSC system is used, an execution of the time-interruption routine is repeated at a regular time-interval of 1/30 sec. Note, the execution of this time-interruption routine is started by selecting the white-balance-adjustment operation mode with the mode-selection switch (SW3) 78 after the power ON/OFF switch (SW1) 74 is turned ON.

At steps 1601, 1602, 1603 and 1604, it is determined whether respective flags F1, F2, F3 and F4 are "0" in sequence. At an initial stage, since all of the flags F1, F2, F3 and F4 are "0", the control proceeds to step 1605, in which the switching circuit 66 is operated so that the histogram-generating circuit 64 is connected to the frame memory 36. Namely, the connection of the histogram-generating circuit 64 is switched from the video-process circuit 38 to the frame memory 36.

At step 1606, it is determined whether the lamp ON/OFF switch (SW3) 78 is turned ON. When the lamp ON/OFF switch (SW3) 78 is OFF, the routine once ends. Although the routine is repeatedly executed at the regular interval of the given time (1/30 sec or 1/25 sec), there is no progress as long as the lamp ON/OFF switch (SW3) 78 is OFF. Namely, at step 1606, it is monitored whether the lamp ON/OFF switch (SW3) 78 is turned ON.

When it is confirmed that the lamp ON/OFF switch (SW3) 78 is turned ON at step 1606, the control proceeds to step 1607, in which it is determined whether a predetermined time has elapsed. Although the routine is repeatedly executed at the regular interval of the given time, there is no progress until the predetermined time has elapsed. As is well known, just after the white-light lamp 18, such as a halogen lamp, a xenon lamp or the like, is lit, an emission of light from the lamp 18 is unstable. Accordingly, the predetermined time is set as a time necessary to allow the emission of light from the lamp 18 to become stabilized.

When it is confirmed that the predetermined time has elapsed at step 1607, the control proceeds to step 1608, in which the message "ADJUSTMENT FOR WHITE BALANCE IS POSSIBLE" is displayed on the monitor 40. Namely, as mentioned above, the fixed character code data, corresponding to the message "ADJUSTMENT FOR WHITE BALANCE IS POSSIBLE" is read from the ROM of the system control circuit 30, and is then written to the VRAM of the character-generating circuit 68, whereby the display of the message "ADJUSTMENT FOR WHITE BALANCE IS POSSIBLE" on the monitor 40 is performed.

At step 1609, it is determined whether a flexible scope (10) to be subjected to a white balance readjustment is connected to the video-signal processing unit 12. When the flexible scope (10) concerned is not connected to the video-signal processing unit 12, the control proceeds from step 1609 to step 1610, in which the flag F4 is made to be "1". Then, the routine once ends. Namely, at step 1609, it is monitored whether the flexible scope (10) concerned is connected to the video-processing unit 12, and there is no progress until the connection of the flexible scope (10) to the video-signal processing unit 12 is confirmed (F4=1).

At step 1609, when the connection of the flexible scope (10) to the video-signal processing unit 12 is confirmed, the control proceeds from step 1609 to step 1611, in which red, green and blue correction factors $R_{GAIN}$, $G_{GAIN}$ and $B_{GAIN}$ are read from an EEPROM (70) of the flexible scope (10) concerned, and then are temporarily stored in the RAM of the system control circuit 30. Then, at step 1612, the flag F3 is made to be "1".

At step 1613, it is determined whether the white-balance adjustment initiation switch (SW4) 80 is turned ON. Namely, at step 1613, it is monitored whether the initiation switch (SW4) 80 is turned ON, and there is no progress until the turning-ON of the initiation switch (SW4) 80 is confirmed (F3=1). An operation of the initiation switch (SW4) 80 is obligatory after a preparation for the white-balance readjustment is completed. Namely, the distal end of the flexible scope (10) concerned is inserted into a tubular-like envelope, an inner wall surface of which is coated with a standard white pigment layer, and the initiation switch (SW4) 80 must be operated after the insertion of the distal end of the flexible scope (10) into the tubular-like envelope is completed.

Note, after the insertion of the distal end of the flexible scope (10) into the tubular-like envelope, a frame of red image-pixel signals, a frame of green image-pixel signals and a frame of blue image-pixel signals, which are derived from the standard white pigment layer of the envelope, are successively read from a CCD image sensor (14) of the flexible scope (10) concerned, and a red histogram, a green histogram and a blue histogram are successively generated in the histogram-generating circuit 64 on the basis of the frames of red, green and blue image-pixel signals, respectively.

Also, note, the respective frames of red, green and blue image-pixel signals, read from the CCD image sensor (14), are subjected to the white-balance correction processing in the image-signal processing circuit 32 on the basis of the red, green and blue correction factors $R_{GAIN}$, $G_{GAIN}$ and $B_{GAIN}$ temporarily stored in the RAM of the system control circuit 30.

At step 1613, when the turning-ON of the initiation switch (SW4) 80 is confirmed, the control proceeds from step 1613 to step 1614, in which an average green-gain-value AG is calculated from all of the green image-pixel signals included in the green histogram generated in the histogram-generating circuit 64 as follows:

$$AG = \frac{\sum_{n=0}^{n=255} GL_n * GS_n}{TP}$$

Herein:
  $GL_n$ is a green gain level-value corresponding to a green gain level n (n=0, 1, . . . , 254, 255) of the green histogram;
  $GS_n$ is a number (frequency) of green image-pixel signals exhibiting the green gain level n; and
  TP is a total number of green image-pixel signals included in the green histogram.

At step 1615, an average blue-gain-value AB is calculated from all of the blue image-pixel signals included in the blue histogram generated in the histogram-generating circuit 64 as follows:

$$AB = \frac{\sum_{n=0}^{n=255} BL_n * BS_n}{TP}$$

Herein:
  $BL_n$ is a blue gain level-value corresponding to a blue gain level n (=0, 1, . . . , 254 and 255) of the blue histogram;
  $BS_n$ is a number (frequency) of blue image-pixel signals exhibiting the blue gain level n; and
  TP is a total number of blue image-pixel signals included in the blue histogram.

At step 1616, a difference $\Delta GB$ is calculated between the average green-gain-level value AG and the average blue-gain-level value AB as follows:

$$\Delta GB \leftarrow |AG - AB|$$

Then, at step 1617, it is determined whether the difference $\Delta GB$ is larger than a predetermined permissible value PV. If $\Delta GB > PV$, the control proceeds from step 1617 to step 1618, in which it is determined whether the average blue-gain-level value AB is larger than the average green-gain-level value AG.

If AB>AG, the control proceeds from step 1618 to step 1619, in which a predetermined small value α is subtracted from the blue correction factor $B_{GAIN}$. On the other hand, if AB<AG, the control proceeds from step 1618 to step 1620, in which the predetermined small value α is added to the blue correction factor $B_{GAIN}$. In any event, after either the subtraction or the addition is completed, the routine once ends.

Thereafter, either the subtraction (step 1619) or the addition (step 1620) is repeatedly performed (F3=1) until it is confirmed at step 1617 that the difference $\Delta B$ becomes smaller than the predetermined permissible value PV. At step 1617, if $\Delta GB < PV$, the control proceeds from step 1617 to step 1621, in which the flag F2 is made to be "1".

At step 1622, an average green-gain-value AG is calculated from all of the green image-pixel signals included in the green histogram generated in the histogram-generating circuit 64 in the same manner as at step 1614.

At step 1623, an average red-gain-value AR is calculated from all of the red image-pixel signals included in the red histogram generated in the histogram-generating circuit 64 as follows:

$$AR = \frac{\sum_{n=0}^{n=255} RL_n * RS_n}{TP}$$

Herein:
  $RL_n$ is a red gain level-value corresponding to a red gain level n (=0, 1, . . . , 254 and 255) of the red histogram;
  $RS_n$ is a number (frequency) of red image-pixel signals exhibiting the red gain level n; and
  TP is a total number of red image-pixel signals included in the red histogram.

At step 1624, a difference $\Delta GR$ is calculated between the average green-gain-level value AG and the average red-gain-level value AR as follows:

$$\Delta GR \leftarrow |AG - AR|$$

Then, at step 1625, it is determined whether the difference $\Delta GR$ is larger than the predetermined permissible value PV. If $\Delta GR > PV$, the control proceeds from step 1625 to step 1626, in which it is determined whether the average red-gain-level value AR is larger than the average green-gain-level value AG.

If AR>AG, the control proceeds from step 1626 to step 1627, in which the predetermined small value α is subtracted from the red correction factor $R_{GAIN}$. On the other hand, if AR<AG, the control proceeds from step 1626 to step 1628, in which the predetermined small value α is added to the red correction factor $R_{GAIN}$. In any event, after either the subtraction or the addition is completed, the routine once ends.

Thereafter, either the subtraction (step 1627) or the addition (step 1628) is repeatedly performed (F3=1) until it is confirmed at step 1625 that the difference $\Delta GR$ becomes smaller than the predetermined permissible value PV.

At step 1625, if $\Delta GR < PV$, the control proceeds from step 1625 to step 1629, in which the message "ADJUSTMENT OF WHITE BALANCE HAS BEEN COMPLETED" is displayed on the monitor 40. Namely, as mentioned above, the fixed character code data, corresponding to the message "ADJUSTMENT OF WHITE BALANCE HAS BEEN COMPLETED" is read from the ROM of the system control circuit 30, and is then written to the VRAM of the character-generating circuit 68, whereby the display of the message "ADJUSTMENT OF WHITE BALANCE HAS BEEN COMPLETED" on the monitor 40 is performed.

At step 1630, the adjusted correction factors $R_{GAIN}$, $G_{GAIN}$ and $B_{GAIN}$ are overwritten on the old correction factors $R_{GAIN}$, $G_{GAIN}$ and $B_{GAIN}$ stored in the EEPROM (70) of the flexible scope (10) concerned. Note, as mentioned above, since the red and blue correction factors $R_{GAIN}$ and $B_{GAIN}$ are readjusted with respect to the green correction factor $G_{GAIN}$, only the adjusted correction factors $R_{GAIN}$ and $B_{GAIN}$ may need to be overwritten on the old correction factors $R_{GAIN}$ and $B_{GAIN}$.

At step 1631, it is determined whether the flexible scope (10) concerned has been disconnected from the video-signal processing unit 12. When the flexible scope (10) concerned has not been disconnected from the video-signal processing unit 12, the control proceeds from step 1631 to step 1632, in which the flag F1 is made to be "1". Then, the routine once ends. Thereafter, although the routine is repeatedly executed at the regular interval of the given time, there is no progress until the flexible scope (10) concerned is disconnected from the video-signal processing unit 12 (F1=1).

At step 1631, when the disconnection of the flexible scope (10) from the video-signal processing unit 12 is confirmed, the control proceeds from step 1631 to step 1633, in which the three flags F1, F2 and F3 are made to be "0". Then, the routine once ends.

Thereafter, at step 1609, it is monitored whether another flexible scope (10) to be subjected to a white balance readjustment of is connected to the video-signal processing unit 12 (F4=1). Of course, at step 1609, when the connection of the other flexible scope (10) to the video-signal processing unit 12 is confirmed, a readjustment of red, green and blue correction factors $R_{GAIN}$, $G_{GAIN}$ and $B_{GAIN}$ thereof is performed in the same manner as mentioned above.

On the other hand, when the usual operation mode is selected by the mode-selection switch (SW3) 78 during the monitoring of the connection of the other flexible scope (10) to the video-signal processing unit 12, the execution of the routine completely ends, and the flag 4 is made to be "0".

Note, for the readjustment of the color correction factors $R_{GAIN}$, $G_{GAIN}$ and $B_{GAIN}$, color difference signals may be utilized in place of the color (red, green and blue) image-pixel signals.

As is apparent from the foregoing, the white-balance adjustment routine is executed by selecting the white-balance-adjustment operation mode with the mode-selection switch (SW3) 78, and each of the average red, green and blue gain level-values AR, AG and AB is calculated without thinning the corresponding monochromatic image-pixel signals included in the corresponding monochromatic histogram.

Although the present invention is described with respect to the electronic endoscope using the RGB field sequential-type color imaging system, the present invention is applicable to any other electronic endoscope featuring by a CCD image sensor with an RGB color filter.

Finally, it will be understood by those skilled in the art that the foregoing description is of preferred embodiments of the device, and that various changes and modifications may be made to the present invention without departing from the spirit and scope thereof.

The present disclosure relates to subject matters contained in Japanese Patent Application No. 10-174417 (filed on Jun. 22, 1998) which is expressly incorporated herein, by reference, in its entirety.

What is claimed is:

1. An electronic endoscope comprising:
   a flexible scope having an image sensor provided at a distal end of said scope, and an optical light guide extending through said scope;
   a video-signal processing unit, to which a proximal end of said flexible scope is detachably connected, that processes image-pixel signals successively read from said image sensor;
   a light source provided in said video-signal processing unit such that light, emitted from said light source, is guided through said optical light guide and radiates from the distal end of said flexible scope;
   a light-emission regulator associated with said light source that regulates the radiation of light from the distal end of said flexible scope;
   a histogram generator that successively generates a luminance-signal-histogram in accordance with said processed image-pixel signals;
   an approximate-calculator that approximately calculates an approximate average luminance level-value in accordance with luminance signals exhibiting thinned luminance levels extracted from said luminance-signal-histogram; and
   a controller that controls said light-emission regulator in accordance with said approximate average luminance level-value, such that an image having a constant brightness level is reproduced in accordance with said processed image-pixel signals.

2. An electronic endoscope as set forth in claim 1, wherein said generation of said luminance-signal-histogram by said histogram generator is based on a frame of image-pixel signals extracted from said processed image-pixel signals.

3. An electronic endoscope as set forth in claim 1, wherein said generation of said luminance-signal-histogram by said histogram generator is based on a field of image-pixel signals extracted from said processed image-pixel signals.

4. An electronic endoscope as set forth in claim 1, wherein said thinned luminance levels are extracted from said luminance-signal-histogram at regular intervals.

5. An electronic endoscope as set forth in claim 4, wherein said thinned luminance levels are alternately extracted from said luminance-signal-histogram.

6. An electronic endoscope as set forth in claim 1, wherein said approximate calculation of said average luminance level-value by said calculator is performed over a restricted range of a full histogram-definition range of said luminance-signal-histogram, and said restricted range is defined in accordance with another luminance-signal-histogram generated in said histogram-generator prior to the generation of said luminance-signal-histogram.

7. An electronic endoscope as set forth in claim 1, wherein said approximate calculation of said average luminance level-value by said calculator is performed over a restricted range of a full histogram-definition range of said luminance-signal-histogram, and said restricted range is obtained by marginally extending a histogram range defined by a minimum luminance level and a maximum luminance level of another luminance-signal-histogram generated in said histogram-generator prior to said generation of said luminance-signal-histogram.

8. An electronic endoscope as set forth in claim 1, further comprising an exact-calculator that periodically and exactly calculates an exact average luminance level-value in accordance with luminance signals included in said luminance-signal-histogram, said controller periodically controlling said light-emission regulator in accordance with said exact average luminance level-value.

9. An electronic endoscope as set forth in claim 1, wherein said image sensor is constituted so as to successively generate a first frame of monochromatic image-pixel signals, a second frame of monochromatic image-pixel signals and a third frame of monochromatic image-pixel signals; said flexible scope further has a memory that stores a first gain-correction factor, a second gain-correction factor and a third gain-correction factor; said video-signal processing unit is constituted so as to read said first, second and third gain-correction factors from said memory when said flexible scope is connected to said unit, and so as to process said first, second and third frames of monochromatic image-pixel signals with said first, second and third gain-correction factors, respectively; and said histogram generator is constituted so as to successively generate a first image-pixel-signal-histogram, a second image-pixel-signal-histogram and a third image-pixel-signal-histogram in accordance with said first, second and third frames of monochromatic image-pixel signals, processed with said first gain-correction factor, said second gain-correction factor and said third correction factor, respectively, when a gain-correction factor adjustment mode is selected, said endoscope further comprising:

a first calculator that calculates a first average signal-level-value in accordance with image-pixel signals included in said first image-pixel-signal-histogram;

a second calculator that calculates a second average signal-level-value in accordance with image-pixel signals included in said second image-pixel-signal-histogram;

a third calculator that calculates a third average signal-level-value in accordance with image-pixel signals included in said third image-pixel-signal-histogram; and a gain-correction-factor adjuster that adjusts at least two of said first, second and third gain-correction factors such that said first, second and third average signal-level-values are substantially equal to each other.

10. An electronic endoscope as set forth in claim 9, further comprising a writer that writes said adjusted gain-correction factors in the memory of said flexible scope.

11. An electronic endoscope as set forth in claim 9, further comprising an operation-mode selector that switches an operation mode of said endoscope from a usual-operation mode to said gain-correction factor adjustment mode, the adjustment of said gain-correction factors by said gain-correction-factor adjuster being performed when said gain-correction factor adjustment mode is selected by said operation-mode selector.

* * * * *